(12) United States Patent
Sarkar et al.

(10) Patent No.: US 9,713,701 B2
(45) Date of Patent: Jul. 25, 2017

(54) USING MULTIPLE DIAGNOSTIC PARAMETERS FOR PREDICTING HEART FAILURE EVENTS

(75) Inventors: Shantanu Sarkar, Roseville, MN (US); Douglas A. Hettrick, Andover, MN (US); Robert W. Stadler, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 1459 days.

(21) Appl. No.: 12/184,003

(22) Filed: Jul. 31, 2008

(65) Prior Publication Data
US 2010/0030293 A1 Feb. 4, 2010

(51) Int. Cl.
A61N 1/365 (2006.01)
A61M 37/00 (2006.01)
(Continued)

(52) U.S. Cl.
CPC ............. *A61M 37/00* (2013.01); *A61B 5/046* (2013.01); *A61B 5/0464* (2013.01);
(Continued)

(58) Field of Classification Search
USPC ........ 600/508, 377, 506, 301; 607/18, 28, 1; 604/66
See application file for complete search history.

(56) References Cited

U.S. PATENT DOCUMENTS 4,374,382 A 2/1983 Markowitz
4,823,797 A 4/1989 Heinze et al.
(Continued)

FOREIGN PATENT DOCUMENTS

DE 10148440 A1 4/2003
EP 1997427 A1 4/2008
(Continued)

OTHER PUBLICATIONS

International Preliminary Report on Patentability from international application No. PCT/US2008/009307, dated Feb. 10, 2011, 7 pp.
Adamson et al, "Continuous Autonomic Assessment in Patients with Symptomatic Heart Failure . . . " Circulation Journal of American Heart Association, pp. 2389-2394, 110:16, Lippincott Williams & Wilkins, Baltimore MD, 2004.
Lusignan, et al. "Compliance and Effectiveness of 1 Year's Home Telemonitoring. The Report of a Pilot Study . . . " European Journal of Heart Failure, 3:723-730, 2001.
(Continued)

*Primary Examiner* — Alyssa M Alter
(74) *Attorney, Agent, or Firm* — Shumaker & Sieffert, P.A.

(57) ABSTRACT

Techniques for using multiple physiological parameters to provide an early warning for worsening heart failure are described. A medical device monitors a primary diagnostic parameter that is indicative of worsening heart failure, such as intrathoracic impedance or pressure, and one or more secondary diagnostic parameters. The medical device detects worsening heart failure in the patient based on the primary diagnostic parameter when an index that is changed over time based on the primary diagnostic parameter value is outside a range of values, termed the threshold zone. When the index is within the threshold zone, the medical device detects worsening heart failure in the patient based on the one or more secondary diagnostic parameters. Upon detecting worsening heart failure, the medical device may, for example, provide an alert that enables the patient to seek medical attention before experiencing a heart failure event.

43 Claims, 17 Drawing Sheets

(51) Int. Cl.
*A61B 5/046* (2006.01)
*A61B 5/0464* (2006.01)
*A61B 5/053* (2006.01)
*A61B 5/11* (2006.01)

(52) U.S. Cl.
CPC .......... *A61B 5/0537* (2013.01); *A61B 5/0538* (2013.01); *A61B 5/1118* (2013.01); *A61B 2562/0219* (2013.01); *A61N 1/36585* (2013.01)
USPC .............................. 607/18; 600/301; 604/66

(56) References Cited

U.S. PATENT DOCUMENTS

| | | | |
|---|---|---|---|
| 5,107,833 A | 4/1992 | Barsness | |
| 5,117,824 A | 6/1992 | Keimel et al. | |
| 5,168,871 A | 12/1992 | Grevious | |
| 5,271,395 A | 12/1993 | Wahlstrand et al. | |
| 5,292,343 A | 3/1994 | Blanchette et al. | |
| 5,314,450 A | 5/1994 | Thompson | |
| 5,324,315 A | 6/1994 | Grevious | |
| 5,354,319 A | 10/1994 | Wyborny et al. | |
| 5,383,909 A | 1/1995 | Keimel | |
| 5,545,186 A | 8/1996 | Olson et al. | |
| 5,749,367 A | 5/1998 | Gamlyn et al. | |
| 5,755,736 A | 5/1998 | Gillberg et al. | |
| 5,836,975 A | 11/1998 | DeGroot | |
| 5,876,353 A | 3/1999 | Riff | |
| 5,957,861 A | 9/1999 | Combs et al. | |
| 6,045,513 A | 4/2000 | Stone et al. | |
| 6,102,874 A | 8/2000 | Stone et al. | |
| 6,104,949 A | 8/2000 | Crick et al. | |
| 6,148,233 A | 11/2000 | Owen et al. | |
| 6,154,674 A | 11/2000 | Meier | |
| 6,221,011 B1 | 4/2001 | Bardy | |
| 6,263,243 B1 | 7/2001 | Lang | |
| 6,277,072 B1 | 8/2001 | Bardy | |
| 6,280,380 B1 | 8/2001 | Bardy | |
| 6,280,409 B1 | 8/2001 | Stone et al. | |
| 6,336,903 B1* | 1/2002 | Bardy ........................... | 600/508 |
| 6,405,085 B1 | 6/2002 | Graupner et al. | |
| 6,449,509 B1 | 9/2002 | Park et al. | |
| 6,459,929 B1 | 10/2002 | Hopper et al. | |
| 6,463,326 B1 | 10/2002 | Hartley et al. | |
| 6,473,640 B1 | 10/2002 | Erlebacher | |
| 6,480,733 B1 | 11/2002 | Turcott | |
| 6,512,949 B1 | 1/2003 | Combs et al. | |
| 6,572,557 B2 | 6/2003 | Tchou et al. | |
| 6,595,927 B2 | 7/2003 | Pitts-Crick et al. | |
| 6,671,549 B2 | 12/2003 | Van Dam et al. | |
| 6,821,249 B2 | 11/2004 | Casscells, III et al. | |
| 6,829,503 B2 | 12/2004 | Alt | |
| 6,866,629 B2 | 3/2005 | Bardy | |
| 6,895,275 B2 | 5/2005 | Markowitz et al. | |
| 6,907,288 B2 | 6/2005 | Daum | |
| 6,913,577 B2 | 7/2005 | Bardy | |
| 6,931,272 B2 | 8/2005 | Burnes | |
| 6,945,934 B2 | 9/2005 | Bardy | |
| 6,960,167 B2 | 11/2005 | Bardy | |
| 7,127,290 B2 | 10/2006 | Girouard et al. | |
| 7,177,681 B2 | 2/2007 | Zhu et al. | |
| 7,184,821 B2 | 2/2007 | Belalcazar et al. | |
| 7,248,916 B2 | 7/2007 | Bardy | |
| 7,272,442 B2 | 9/2007 | Freeberg | |
| 7,272,443 B2 | 9/2007 | Min et al. | |
| 7,308,309 B1 | 12/2007 | Koh | |
| 7,310,551 B1 | 12/2007 | Koh et al. | |
| 7,313,434 B2 | 12/2007 | Belalcazar et al. | |
| 7,340,296 B2 | 3/2008 | Stahmann et al. | |
| 7,387,610 B2 | 6/2008 | Stahmann et al. | |
| 7,389,143 B2 | 6/2008 | Hopper et al. | |
| 8,055,335 B2 | 11/2011 | Stylos | |
| 8,180,440 B2 | 5/2012 | Mccombie et al. | |
| 8,255,046 B2* | 8/2012 | Sarkar et al. ................. | 600/547 |
| 8,271,072 B2 | 9/2012 | Houben et al. | |
| 8,632,473 B2* | 1/2014 | Sowelam ....................... | 600/538 |
| 8,744,565 B2 | 6/2014 | Zielinski et al. | |
| 2001/0011153 A1 | 8/2001 | Bardy | |
| 2001/0021801 A1 | 9/2001 | Bardy | |
| 2001/0039504 A1 | 11/2001 | Linberg et al. | |
| 2002/0026104 A1 | 2/2002 | Bardy | |
| 2002/0147475 A1 | 10/2002 | Scheiner et al. | |
| 2003/0028221 A1 | 2/2003 | Zhu et al. | |
| 2003/0055461 A1 | 3/2003 | Girouard et al. | |
| 2003/0125611 A1 | 7/2003 | Bardy | |
| 2003/0149367 A1 | 8/2003 | Kroll et al. | |
| 2003/0220580 A1 | 11/2003 | Alt | |
| 2004/0102712 A1 | 5/2004 | Belalcazar et al. | |
| 2004/0122484 A1* | 6/2004 | Hatlestad et al. ............. | 607/60 |
| 2004/0148140 A1 | 7/2004 | Tarassenko et al. | |
| 2004/0167580 A1 | 8/2004 | Mann et al. | |
| 2004/0172080 A1* | 9/2004 | Stadler et al. ................. | 607/17 |
| 2005/0124908 A1 | 6/2005 | Belalcazar et al. | |
| 2006/0020295 A1 | 1/2006 | Brockway et al. | |
| 2006/0094967 A1 | 5/2006 | Bennett et al. | |
| 2006/0224190 A1 | 10/2006 | Gill et al. | |
| 2006/0293609 A1 | 12/2006 | Stahmann et al. | |
| 2007/0021678 A1 | 1/2007 | Beck et al. | |
| 2007/0142732 A1 | 6/2007 | Brockway et al. | |
| 2007/0156061 A1 | 7/2007 | Hess | |
| 2007/0203423 A1 | 8/2007 | Bardy | |
| 2008/0024293 A1 | 1/2008 | Stylos | |
| 2008/0027349 A1 | 1/2008 | Stylos | |
| 2008/0082001 A1 | 4/2008 | Hatlestad et al. | |
| 2008/0161657 A1 | 7/2008 | Kessels et al. | |
| 2008/0162182 A1 | 7/2008 | Cazares et al. | |
| 2008/0162812 A1 | 7/2008 | Stroberger et al. | |
| 2010/0030292 A1 | 2/2010 | Sarkar et al. | |
| 2010/0030293 A1 | 2/2010 | Sarkar et al. | |
| 2010/0114241 A1 | 5/2010 | Donofrio et al. | |
| 2010/0198097 A1 | 8/2010 | Sowelam | |
| 2010/0305641 A1 | 12/2010 | Pillai et al. | |
| 2012/0221066 A1 | 8/2012 | Rosenberg et al. | |
| 2015/0230722 A1 | 8/2015 | Sarkar et al. | |

FOREIGN PATENT DOCUMENTS

| | | |
|---|---|---|
| EP | 2 143 467 A1 | 1/2010 |
| WO | 9833554 A1 | 8/1998 |
| WO | 0064336 A1 | 11/2000 |
| WO | 0132260 A1 | 5/2001 |
| WO | 2006070124 A1 | 7/2006 |
| WO | 2006/081432 A1 | 8/2006 |
| WO | WO2006/081432 A1 | 8/2006 |
| WO | 2007079354 A2 | 7/2007 |
| WO | 2008054580 A2 | 5/2008 |
| WO | 2009035596 A1 | 3/2009 |

OTHER PUBLICATIONS

Baer, et al. "Electronic Home Monitoring of Congestive Heart Failure Patients: Design and Feasibility", Congestive Heart Failure, 5:105-113, 1999.
Wuerz & Meador, "Effects of Prehospital Medications on Mortality and Length of Stay in Congestive Heart Failure", Annals of Emergency Medicine 21:6 pp. 669-674, Jun. 1992.
U.S. Appl. No. 12/112,765, filed Apr. 30, 2008 by Todd M. Zielinski et al.—client reference No. P0024382.00.
International Search Report and Written Opinion from corresponding PCT Application Serial No. PCT/US2008/009307, mailed May 8, 2009 (11 pgs.).
Office Action from U.S. Appl. No. 12/184,149, dated Apr. 7, 2011, 7 pp.
Response to Office Action dated Apr. 7, 2011, from U.S. Appl. No. 12/184,149, filed Jul. 7, 2011, 20 pp.
Response to Final Office Action dated May 9, 2012, from U.S. Appl. No. 12/363,264, filed Jul. 9, 2012, 6 pp.
Advisory Action from U.S. Appl. No. 12/363,264, dated Jul. 20, 2012, 3 pp.
Response to Office Action dated Jan. 27, 2012, from U.S. Appl. No. 12/184,149, filed Apr. 25, 2012, 13 pp.
Office Action from U.S. Appl. No. 12/184,149, dated Jan. 27, 2012, 7 pp.

(56) References Cited

OTHER PUBLICATIONS

Response to Office Action dated Nov. 30, 2011, from U.S. Appl. No. 12/363,264, filed Feb. 29, 2012, 9 pp.
Communication of a Notice of Opposition; European Patent Office; Application No. 08794965.7; Dated: Apr. 11, 2013; 33 pages.
Abraham, William T. et al., "Intrathoracic Impedance Monitoring for Early Detection of Impending Heart Failure Decompensation"; Congestive Heart Failure; Mar./Apr. 2007; pp. 113-115.
Maisel, Alan, "Algorithms for Using B-Type Natriuretic Peptide Levels in the Diagnosis and Management of Congestive Heart Failure"; Critical Pathways in Cardiology; vol. 1, No. 2, 2002; pp. 67-73.
Office Action from U.S. Appl. No. 12/363,264, dated May 9, 2012, 9 pp.
Office Action from U.S. Appl. No. 12/184,149, dated Sep. 30, 2011, 6 pp.
Response to Office Action dated Sep. 30, 2011, from U.S. Appl. No. 12/184,149, filed Dec. 12, 2011, 14 pp.
Office Action from U.S. Appl. No. 12/363,264, dated Nov. 30, 2011, 5 pp.
Adamson et al, "Continuous Autonomic Assessment in Patients with Symptomatic Heart Failure . . ." Circulation Journal of America Heart Association, pp. 2389-2394, 110:16, Lippincott Williams & Wilkins, Baltimore MD, 2004.
Lusignan, et al. "Compliance and Effectiveness of 1 Year's Home Telemonitoring. The Report of a Pilot Study . . ." European Journal of Heart Failure, 3:723-730, 2001.
Baer, et al "Electronic Home Monitoring of Congestive Heart Failure Patients: Design and Feasibility", Congestive Heart Failure, 5:105-113, 1999.
Wuerz & Meador, "Effects of Prehospital Medications on Mortality and Length of Stay in Congestive Heart Failure", Annuals of Emergency Medicine 21:6 pp. 669-674, Jun. 1992.
Berman et al. "Transthoracic Electrical Impedance as a Guide to Intravascular Overload", Archives Surgery, 102, pp. 61-62 Jan. 1971.
U.S. Appl. No. 12/112,765, filed Apr. 30, 2008 by Todd M. Zielinski et al.—client reference No. P0024382.00, now U.S. Pat. No. 8,744,565 B2, issued Jun. 3, 2014.
International Preliminary Report on Patentability from international application No. PCT/US2008/009307, dated Feb. 10, 2011, 7 pages.
International Search Report and Written Opinion from PCT Application Serial No. PCT/US2010/054539 dated Feb. 4, 2011 (11 pages).
Office Action from U.S. Appl. No. 12/184,149, dated Apr. 7, 2011, 7 pages, now U.S. Pat. No. 8,255,046 B2, issued Aug. 28, 2012.
Response to Office Action dated Apr. 7, 2011, from U.S. Appl. No. 12/184,149, filed Jul. 7, 2011, 20 pages, now U.S. Pat. No. 8,255,046 B2, issued Aug. 28, 2012.
Office Action from U.S. Appl. No. 12/184,149, dated Sep. 30, 2011, 6 pages, now U.S. Pat. No. 8,255,046 B2, issued Aug. 28, 2012.
Response to Office Action dated Sep. 30, 2011, from U.S. Appl. No. 12/184,149, filed Dec. 12, 2011, 14 pages, now U.S. Pat. No. 8,255,046 B2, issued Aug. 28, 2012.
Office Action from U.S. Appl. No. 12/363,264, dated Nov. 30, 2011, 5 pages, now U.S. Pat. No. 8,632,473 B2, issued Jan. 21, 2014.
Office Action from U.S. Appl. No. 12/363,264, dated May 9, 2012, 9 pages, now U.S. Pat. No. 8,632,473 62, issued Jan. 21, 2014.
Abraham, William T. et al., "Intrathoracic Impedance Monitoring for Early Detection of Impending Heart Failure Decompensation", Congestive Heart Failure; Mar./Apr. 2007; pp. 113-115.
Maisel, Alan, "Algorithms for Using B-Type Natriuretic Peptide Levels in the Diagnosis and Management of Congestive Heart Failure", Critical Pathways in Cardiology, vol. 1, No. 2, 2002; pp. 67-73.
Communication of a Notice of Opposition; European Patent Office; Application No. 08794965.7; Dated Nov. 4, 2013; 33 pages.

Office Action from U.S. Appl. No. 12/184,149, dated Jan. 27, 2012, 7 p., now U.S. Pat. No. 8,255,046 B2, issued Aug. 28, 2012.
Response to Office Action dated Nov. 30, 2011, from U.S. Appl. No. 12/363,264, filed Feb. 29, 2012, 9 pp., now U.S. Pat. No. 8,632,473 B2, issued Jan. 21, 2014.
Response to Office Action dated Jan. 27, 2012, from U.S. Appl. No. 12/184,149, filed Apr. 25, 2012, 13 pp. , now U.S. Pat. No. 8,255,046 B2, issued Aug. 28, 2012.
Response to Final Office Action dated May 9, 2012, from U.S. Appl. No. 12/363,264, filed Jul. 9, 2012, 6 pp., now U.S. Pat. No. 8,632,473 B2, issued Jan. 21, 2014.
Advisory Action from U.S. Appl. No. 12/363,264, filed Jul. 20, 2012, 3 pp., now U.S. Pat. No. 8,632,473 B2, issued Jan. 21, 2014.
Further Response by Cardiac Pacemakers, Inc., EP U.S. Pat. No. 2 187 807 B1, Apr. 2, 2014, 15 pages.
Summon to Oral Proceedings and Preliminary Opinion of EPO, Aug. 1, 2014, Application No. 08 794 965.7, 6 pages.
Medtronic, Inc. Reply to Notice of Opposition, Nov. 18, 2013, Opposition to European Patent No. EP 2 187 807 (EP 08794965.7), 16 pages.
Notice of Opposition for EP Application No. 07 812 355.1, Mailed Jun. 26, 2013, 29 pages.
Reply to Notice of Opposition for EP Application No. 07 812 355.1, Mailed Feb. 5, 2014, 16 pages.
Letter with Response of the Patentee and Preliminary Opinion of the Opposition Division for EP Application No. 07 812 355.1 Mailed Nov. 17, 2014. 19 pages.
Preliminary Opinion for EP Application No. 07 812 355.1, Mailed Jun. 13, 2014, 4 pages.
Decision for EP Application No. 07 812 355.1, Mailed Feb. 20, 2015, 11 pages.
Yu et al., "Intrathoracic Impedance Monitoring in Patients with Heart Failure: Correlation with Fluid Status and Feasibility of Early Warning Preceding Hospitalization", Circulation 2005; vol. 112; pp. 841-848; originally published online Aug. 1, 2005.
Excerpt of the web-site "http://rnedical-dictionary,thefreedictionary. com/hysteresis" referring to the definition of the term "hysteresis" in cardiac pacemakers, 5 pages.
Excerpt of the textbook "Analog Signal Processing" - Ramon Pallas-Areny, John G. Webster, John Wiley and Sons, 1999, 3 pages.
Excerpt of the textbook "Ops Amps: Design, Applications, and Troubleshooting" - David L. Terrell, Newnes, 1996, 5 pages.
Excerpt of the textbook "Radius: Image Understanding for Imagery Intelligence" —Oscar Firschein, Thomas M. Strat, Morgan Kaufmann, 1997, 1 page.
Excerpt of the textbook Programmable Controllers: An Engineer's Guide—E.A. Parr, Newnes, 2003, 1 page.
Opposition Decision, Feb. 20, 2015, EP Application No. 07 812 355.1, 11 pages.
Response to Preliminary Opinion of the Opposition Division, Mar. 30, 2015, EP Application No. 08 79 4965.7/2187807, 17 pages.
Notice of Appeal in Opposition U.S. Pat. No. 2,187,807 filed Sep. 1, 2015 by Cardiac Pacemakers, Inc., 9 pages.
Rejection of Opposition U.S. Pat. No. 2,187,807, filed Jun. 8, 2015 by Opposition Court, 15 pages.
Decision rejecting the Opposition U.S. Pat. No. 2,187,807, filed Jun. 24, 2015, 26 pages. Jun. 2, 2016.
Office Action from U.S. Appl. No. 14/629,027, dated Jul. 28, 2016, 11 pp.
Prosecution History from U.S. Appl. No. 12/184,149, dated from Apr. 7, 2011 through Jul. 26, 2012, 76 pp.
Prosecution History from U.S. Appl. No. 12/363,264, dated from Nov. 30, 2011 through Sep. 16, 2013, 41 pp.
Notice of Allowance from U.S. Appl. No. 12/768,384, dated Jun. 19, 2012, 6 pp.
Office Action dated Jul. 28, 2016, from U.S. Appl. No. 14/629,027, filed Dec. 28, 2016, 13 pp.

* cited by examiner

USING MULTIPLE DIAGNOSTIC PARAMETERS FOR PREDICTING HEART FAILURE EVENTS

TECHNICAL FIELD

The invention relates to medical devices and, more particularly, devices for the diagnosis of worsening heart failure and treatment of related ailments.

BACKGROUND

A variety of medical devices have been used or proposed for use to deliver a therapy to and/or monitor a physiological condition of patients. As examples, such medical devices may deliver therapy and/or monitor conditions associated with the heart, muscle, nerve, brain, stomach or other organs or tissue. Medical devices that deliver therapy include medical devices that deliver one or both of electrical stimulation or a therapeutic agent to the patient. Some medical devices are implantable medical devices (IMDs) that are implanted within the patient.

Some medical devices have been used or proposed for use to monitor heart failure or to detect heart failure events. Typically, such medical devices have been implantable and, in many cases, have been cardiac pacemakers, cardioverters and/or defibrillators with added heart failure monitoring functionality. In some cases, such medical devices have monitored heart failure by monitoring intrathoracic impedance, which may provide a good indication of the level of edema in patients. While edema is a sign of many other conditions it is also a sign of worsening heart failure. Worsening heart failure may result in cardiac chamber dilation, increased pulmonary blood volume, and fluid retention in the lungs—all of which contribute to a decrease in intrathoracic impedance. Other diagnostic parameters, such as heart rate variability, have been proposed for use in such devices to identify worsening heart failure or heart failure events.

Generally, the first indication that a physician would have of the occurrence of edema in a patient is not until it becomes a physical manifestation with swelling or breathing difficulties so overwhelming as to be noticed by the patient who then proceeds to be examined by a physician. This is undesirable since hospitalization at such a time would likely be required for a heart failure patient. Accordingly, medical devices have been used to monitor impedance in patients and provide an alert to the patient to seek medical treatment prior to the onset of worsening heart failure with symptoms, such as edema, that require hospitalization.

SUMMARY

This disclosure describes techniques for using multiple diagnostic parameters to provide an early warning for worsening heart failure. A medical device monitors a primary diagnostic parameter and one or more secondary diagnostic parameters indicative of worsening heart failure in the patient. In some examples, the primary diagnostic parameter indicates a level of pulmonary edema, increased ventricular filling pressure, or other morbidities associated with worsening heart failure. Examples of primary diagnostic parameters include intrathoracic impedance or a cardiovascular pressure. The medical device detects worsening heart failure in the patient based on the primary diagnostic parameter when an index that is changed over time based on the primary diagnostic parameter value is outside a range of values, termed the threshold zone. When the index is within the threshold zone, the medical device detects worsening heart failure in the patient based on the one or more secondary diagnostic parameters.

When the index is within the threshold zone, the medical device may look to one or more secondary diagnostic parameters to corroborate the indication of worsening heart failure provided by the primary diagnostic parameter. In this manner, the medical device may more accurately identify instances of worsening heart failure. Upon detecting worsening heart failure, the medical device may, for example, provide an alert that enables the patient to seek medical attention before experiencing a heart failure event. The alert may be communicated directly to the patient or to the clinician through a variety of methods, including audible tones, handheld devices and automatic telemetry to computerized communication network.

The device may be a purely diagnostic device or may be a combination device that monitors diagnostic parameters and delivers therapy. In some embodiments, the medical device may be configured as an implantable medical device (IMD) or an external device. In some cases, an IMD may be implanted subcutaneously. In other examples, a system may include an IMD and a programmer or other external device in communication with the IMD. In such embodiments, the external device may process data received from the IMD to detect worsening heart failure in the patient and/or provide an alert if worsening heart failure is detected.

In operation, the medical device monitors the primary diagnostic parameter to obtain measured values. The medical device also periodically changes a value of an index that indicates worsening heart failure based on the measured values of the primary diagnostic parameter, e.g., based on whether the values of the primary diagnostic parameter are increasing or decreasing. The secondary diagnostic parameter value may not be considered in determining whether to provide an alert of worsening heart failure when the index is outside the threshold zone. If the index is greater than an upper threshold value of the threshold zone, worsening heart failure may be detected and an alert may be provided to the patient. If the index is less than a lower threshold value of the threshold zone, worsening heart failure is not detected and the medical device continues to monitor the primary diagnostic parameter. However, when the index is within the threshold zone, the secondary diagnostic parameter value is used to detect worsening heart failure in the patient. Worsening heart failure is detected when the secondary diagnostic parameter satisfies a corresponding condition.

In some examples, the secondary diagnostic parameters are monitored prior to the index being within the threshold zone. The secondary diagnostic parameters may be monitored prior to the index being in the threshold zone to provide information regarding trends in secondary diagnostic parameters that may be used to determine whether the secondary diagnostic parameters indicate worsening heart failure when the index is within the threshold zone. For example, some devices or systems may begin monitoring one or more secondary diagnostic parameters when the index is greater than a secondary diagnostic parameter threshold. The secondary diagnostic parameter threshold may be less than the lower threshold of the threshold zone, such that the secondary diagnostic parameters may be monitored prior to the index entering the threshold zone. In some examples, the device or system may monitor one or more secondary diagnostic parameters within an observation window defined by the secondary diagnostic parameter threshold and the upper threshold of the index.

Example secondary diagnostic parameters include atrial fibrillation (AF), heart rate during AF, ventricular fibrillation (VF), heart rate during VF, atrial tachyarrhythmia (AT), heart rate during AT, ventricular tachyarrhythmia (VT), heart rate during VT, activity level, heart rate variability, night heart rate, difference between day heart rate and night heart rate, heart rate turbulence, heart rate deceleration capacity, respiratory rate, baroreflex sensitivity, percentage of cardiac resynchronization therapy (CRT) pacing, metrics of renal function, weight, blood pressure, symptoms entered by the patient via a programmer, and patient history, such as medication history, or history of heart failure hospitalizations. In one example, the medical device may monitor one secondary diagnostic parameter and detect worsening heart failure in the patient based on the secondary diagnostic parameter when the index is within the threshold zone. In another example, the device may monitor two or more secondary diagnostic parameters and detect worsening heart failure in the patient when at least one of the secondary diagnostic parameters satisfies a corresponding condition. In another example, the device may monitor two or more secondary diagnostic parameters and detect worsening heart failure in the patient when a chosen combination of the secondary diagnostic parameters satisfies a corresponding condition.

The threshold zone may be static or dynamic. For example, the threshold zone may change as a function of time or based on knowledge of the condition of the patient. In particular, the threshold zone may automatically change as a function of time. In contrast, a clinician or other authorized user may use an external programmer to manually change the threshold zone based on knowledge of the condition of the patient.

In one example, the disclosure provides a method comprising monitoring at least one primary diagnostic parameter and at least one secondary diagnostic parameter of a patient, wherein the primary and secondary diagnostic parameters are associated with worsening heart failure, changing an index value over time based on the primary diagnostic parameter, wherein the index value indicates worsening heart failure of the patient, determining whether worsening heart failure is detected in the patient based on the index when the index is outside of a threshold zone defined by a lower threshold and an upper threshold, and determining whether worsening heart failure is detected in the patient based on the secondary diagnostic parameter when the index is inside the threshold zone.

In another example, the disclosure provides a system comprising at least one sensor and a processor. The processor monitors at least one primary diagnostic parameter and at least one secondary diagnostic parameter of a patient based on at least one signal from the at least one sensor, wherein the primary and secondary diagnostic parameters are associated with worsening heart failure of the patient, changes an index value over time based on the primary diagnostic parameter, wherein the index indicates worsening heart failure in the patient, determines whether worsening heart failure is detected in the patient based on the index when the index is outside of a threshold zone defined by a lower threshold and an upper threshold, and determines whether worsening heart failure is detected in the patient based on the secondary diagnostic parameter when the index is inside the threshold zone.

In another example, the disclosure provides a computer-readable medium comprising instructions that cause a processor to monitor at least one primary diagnostic parameter and at least one secondary diagnostic parameter of a patient, wherein the primary and secondary diagnostic parameters are associated with worsening heart failure, change an index value over time based on the primary diagnostic parameter, wherein the index indicates worsening heart failure in the patient, determine whether worsening heart failure is detected in the patient based on the index when the index is outside of an threshold zone defined by a lower threshold and an upper threshold, and determine whether worsening heart failure is detected in the patient based on the secondary diagnostic parameter when the index is inside the threshold zone.

In another example, the disclosure provides a system comprising means for monitoring at least one primary diagnostic parameter and at least one secondary diagnostic parameter of a patient, wherein the primary and secondary diagnostic parameters are associated with worsening heart failure, means for changing an index value over time based on the primary diagnostic parameter, wherein the index indicates worsening heart failure in the patient, means for determining whether worsening heart failure is detected in the patient based on the index when the index is outside of a threshold zone defined by a lower threshold and an upper threshold, and means for determining whether worsening heart failure is detected in the patient based on the secondary diagnostic parameter when the index is inside the threshold zone.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
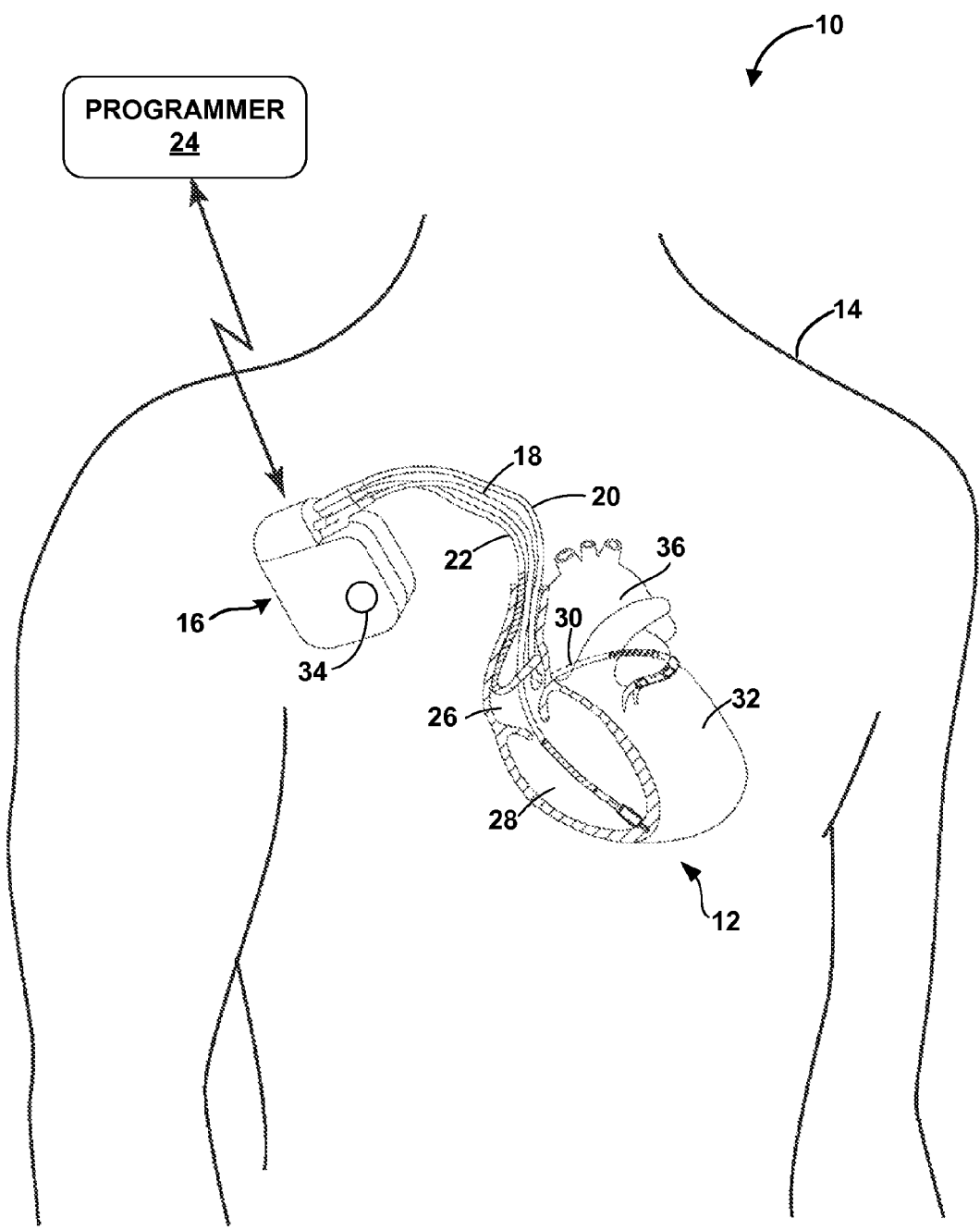
FIG. 1 is a conceptual diagram illustrating an example system that detects worsening heart failure using multiple diagnostic parameters.

FIG. 1 is a conceptual diagram illustrating an example system 10 that may be used to detect worsening heart failure in patient 14 using multiple diagnostic parameters. Generally, system 10 generates an alert in response to detecting worsening heart failure so that patient 14 can seek appropriate treatment before experiencing a heart failure hospitalization (HFH) event. Patient 14 ordinarily, but not necessarily, will be a human.

System 10 includes implantable medical device (IMD) 16, which is coupled to leads 18, 20, and 22, an electrode 34 located on the can of IMD 16, and a programmer 24. In some examples, IMD 16 may be a purely diagnostic device that monitors multiple diagnostic parameters associated with heart failure. In other examples, IMD 16 may additionally operate as a therapy delivery device to deliver electrical signals to heart 12 via one or more of leads 18, 20, and 22, such as an implantable pacemaker, a cardioverter, and/or defibrillator. In some examples, IMD 16 may operate as a drug delivery device that delivers therapeutic substances to patient 14 via catheters (not shown), or as a combination therapy device that delivers both electrical signals and therapeutic substances. Moreover, IMD 16 is not limited to devices implanted as shown in FIG. 1. As an example, IMD 16 may be implanted subcutaneously in patient 14, or may be an entirely external device with leads attached to the skin of patient 14 or implanted percutaneously in patient 14. In some examples, IMD 16 need not include leads, but may include a plurality of electrodes, like electrode 34, on the housing of IMD 16.

In general, IMD 16 monitors a primary diagnostic parameter that is indicative of fluid accumulation and one or more secondary diagnostic parameters. In particular, IMD 16 may monitor the primary diagnostic parameter and the one or more secondary diagnostic parameters at the same time. Example, primary diagnostic parameters include intrathoracic impedance and cardiovascular pressure. Example secondary diagnostic parameters include atrial fibrillation burden (AF), heart rate during AF, ventricular fibrillation burden (VF), heart rate during VF, atrial tachyarrhythmia burden (AT), heart rate during AT, ventricular tachyarrhythmia burden (VT), heart rate during VT, activity level, heart rate variability, night heart rate, difference between day heart rate and night heart rate, heart rate turbulence, heart rate deceleration capacity, respiratory rate, baroreflex sensitivity, percentage of cardiac resynchronization therapy (CRT) pacing, metrics of renal function, weight, blood pressure, symptoms entered by the patient via a programmer, and patient history, such as medication history, or history of heart failure hospitalizations. Thus, IMD 16 may, in various embodiments, monitor either intrathoracic impedance or pressure and one, all, or any combination of the previously recited secondary diagnostic parameters.

IMD 16 detects worsening heart failure in patient 14 based on one or both of the primary diagnostic parameters and the one or more secondary diagnostic parameters. In particular, IMD 16 detects worsening heart failure based only on the primary diagnostic parameter when an index that is changed over time based on the primary diagnostic parameter is outside of a threshold zone. That is, when the index has a value that is greater than the maximum threshold value of the threshold zone, the primary diagnostic parameter may alone be a reliable indicator that patient 14 is experiencing worsening heart failure. When the index has a value that is less than the minimum threshold value of the threshold zone, the primary diagnostic parameter may alone be a reliable indicator that patient 14 is not experiencing worsening heart failure.

If the index is within the threshold zone, then IMD 16 detects worsening heart failure based on the secondary diagnostic parameter. In other words, the threshold zone may be thought of as a "maybe zone" with respect to the primary diagnostic parameter. Accordingly, the secondary diagnostic parameter may be used to provide additional evidence to confirm that patient 14 is or is not experience worsening heart failure, when the index is within the threshold zone. In examples in which system 10 monitors more than one secondary diagnostic parameter, system 10 may detect worsening heart failure when the index is within the threshold zone and one or more of the secondary diagnostic parameters satisfy the corresponding conditions. The number of secondary diagnostic parameters required to must meet the corresponding conditions may be pre-determined and/or selected by a user using programmer 24.

IMD 16 or programmer 24 may be configured to provide an alert in response to detecting worsening heart failure in patient 14. The alert may be audible, visual, or tactile and enables patient 14 to seek medical attention to treat the condition prior to experiencing a heart failure event, or a clinician to direct patient 14 to do so. In some examples, the alert may be a silent alert transmitted to another device associated with a clinician or other user, such as a silent alert transmitted to a server, as described below, and relayed to a physician via a computing device.

In some examples, system 10 may dynamically change the threshold zone over time, i.e., change the values over which the index is conclusive for detecting worsening heart failure. For example, system 10 may automatically increase or decrease the size of the threshold zone as a function of time. The primary diagnostic parameter may become a more reliable indicator of worsening heart failure over time.

In another example, an authorized user may use programmer 24 to manually change the size of the threshold zone. In this way, an authorized user may manually adjust the size of the threshold zone according to the health of patient 14. As an example, if symptoms of patient 14 are worsening, an authorized user may user programmer 24 to decrease the size of the threshold zone.

In the example illustrated in FIG. 1, IMD 16 is configured to monitor intrathoracic impedance and includes leads 18, 20, and 22 extend into the heart 12 of patient 14. Right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12. Other configurations, i.e., number and position of leads, are possible. For example, other leads or lead configurations may be used to monitor pressure and various secondary diagnostic parameters. As described above, in some examples, IMD 16 need not be coupled to leads.

Intrathoracic impedance, as well as various secondary diagnostic parameters, may be measured by creating an electrical path between electrodes (not shown in FIG. 1)

located on one or more of leads 18, 20, and 22 and can electrode 34. In some embodiments, the can of IMD 16 may be used as an electrode in combination with electrodes located on leads 18, 20, and 22. For example, system 10 may measure intrathoracic impedance by creating an electrical path between RV lead 18 and electrode 34. In additional embodiments, system 10 may include an additional lead or lead segment having one or more electrodes positioned at a different location in the cardiovascular system or chest cavity, such as within one of the vena cava, subcutaneously at a location substantially opposite IMD 16 vis-à-vis the thorax of patent 14, or epicardially, for measuring intrathoracic impedance.

In embodiments in which IMD 16 operates as a pacemaker, a cardioverter, and/or defibrillator, IMD 16 may sense electrical signals attendant to the depolarization and repolarization of heart 12 via electrodes coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

It should be understood that IMD 16 may also include other types of sensors for monitoring various other primary and secondary diagnostic parameters, or be coupled to additional medical leads carrying other types of sensors for monitoring other primary and secondary diagnostic parameters. In examples in which IMD 16 monitors pressure as the primary diagnostic parameter, one or more of leads 18, 20, and 22 and/or the device can of IMD 16 may include one or more pressure sensors, such as capacitive pressure sensors. IMD 16 may also include or be coupled to one or more pressure sensors, the output of which may be considered with heart rate to monitor baroreflex sensitivity as a secondary parameter. In another example, system 10 may include one or more accelerometers for monitoring activity of patient 14. In such examples, the accelerometers may be contained within the device can of IMD 16. In some examples, IMD 16 may include or be coupled to one or more sensors, e.g., chemical sensors, pressure sensors, or electrodes for monitoring impedance, to monitor metrics of renal function as one or more secondary diagnostic parameters. In some examples, IMD 16 may use electrodes on leads 18, 20, or 22, or other leads to detect respiration, e.g., based on intrathoracic impedance. In an additional example, IMD 16 may also communicate with an external sensor, such as a scale for monitoring the weight of patient 14. Moreover, in embodiments in which IMD 16 is implemented as an external device (not shown), leads for monitoring primary and secondary diagnostic parameters may be implanted percutaneously in patient 14 or attached to the skin of patient 14.

In some examples, programmer 24 may be a handheld computing device, computer workstation, or networked computing device. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16. The information may relate to the primary and/or secondary diagnostic parameters, i.e., information relating to intrathoracic impedance, pressure, AF burden, heart rate during AF, VF burden, heart rate during VF, AT burden, heart rate during AT, VT burden, heart rate during VT, activity level, heart rate variability, night heart rate, difference between day heart rate and night heart rate, heart rate turbulence, heart rate deceleration capacity, respiratory rate, baroreflex sensitivity, percentage of CRT pacing, metrics of renal function, weight, blood pressure, symptoms entered by the patient via a programmer, and patient history, such as medication history, or history of heart failure hospitalizations. The information may also include trends therein over time. In some embodiments, the user may use programmer 24 to retrieve information from IMD 16 regarding other sensed physiological parameters of patient 14. In addition, the user may use programmer 24 to retrieve information from IMD 16 regarding the performance or integrity of IMD 16 or other components of system 10, such as leads 18, 20, and 22, or a power source of IMD 16.

The user may use programmer 24 to select a primary and one or more secondary diagnostic parameters and program measurement parameters for the selected diagnostic parameters. For example, the user may use programmer 24 to select intrathoracic impedance and/or cardiovascular pressure as the primary diagnostic parameter and to select one or more secondary diagnostic parameters from a list of secondary diagnostic parameters. For example, if the user selects intrathoracic impedance as the primary diagnostic parameter, the user may then use programmer 24 to select electrodes and waveforms for measuring intrathoracic impedance. The user may select or specify measurement parameters for other diagnostic parameters in a similar manner.

In one example, a user may also use programmer 24 to program other parameters related to detecting worsening heart failure, such as parameters associated with the threshold zone. In this case, the user may specify parameters that define the threshold zone, i.e., the values over which the fluid index is inconclusive, or parameters that control how the threshold zone changes over time. Furthermore, the user may use programmer 24 to enter clinical information that can be used as secondary parameters, such as patient history, medication history, history of heart failure hospitalizations, or other historical or current observations of patient condition.

Programmer 24 may also be used to program a therapy progression, select electrodes to deliver defibrillation pulses, select waveforms for the defibrillation pulse, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
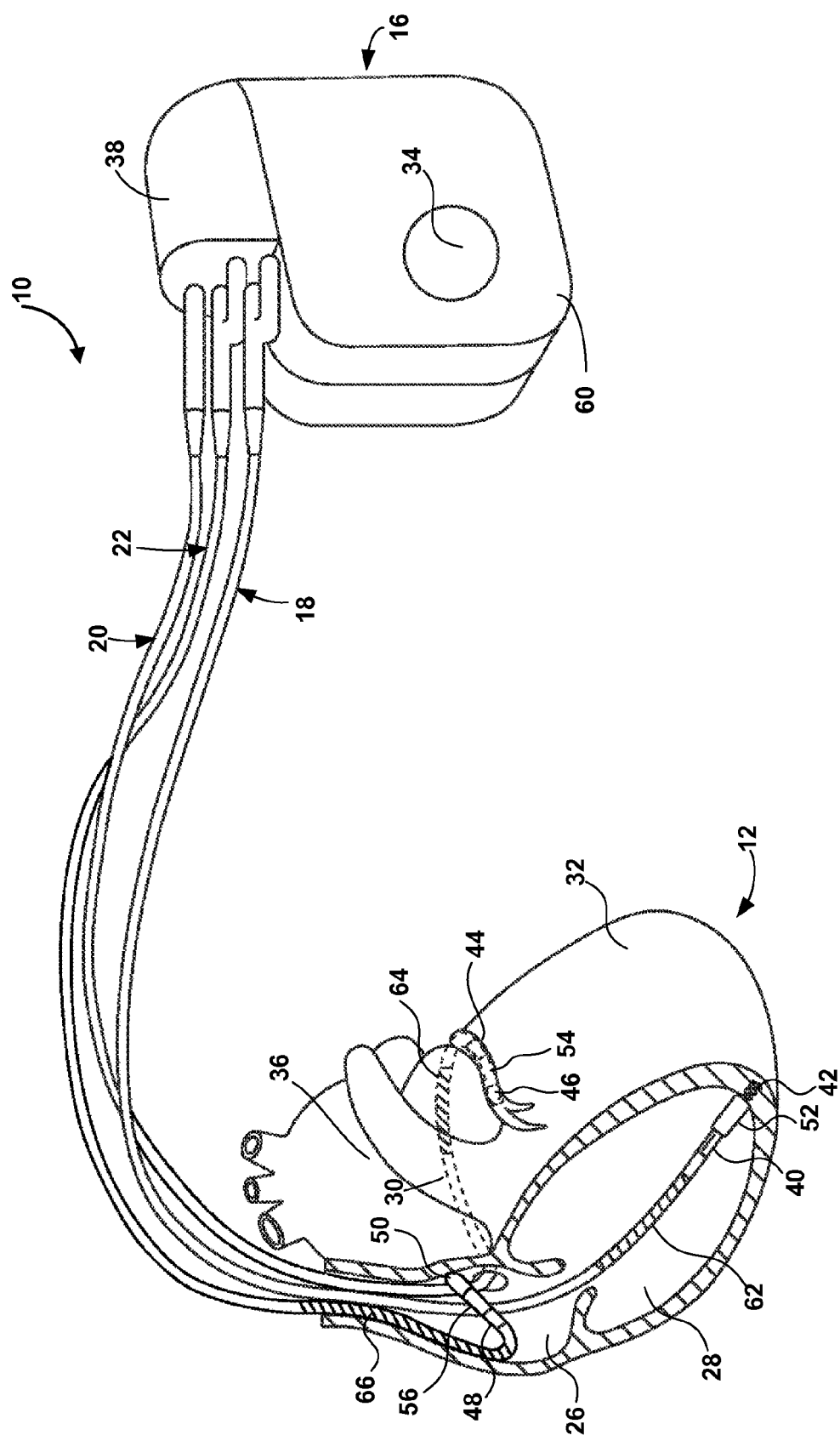
FIG. 2 is a conceptual diagram illustrating the implantable medical device (IMD) and leads of the system shown in FIG. 1 in greater detail.

FIG. 2 is a conceptual diagram illustrating IMD 16, leads 18, 20, and 22, and electrode 34 of system 10 in greater detail. System 10 is generally described in this disclosure as a therapy system that detects worsening heart failure in patient 14 and delivers corrective electrical signals to heart 12. In particular, system 10 is as a therapy system that monitors intrathoracic impedance of tissue in the body of patient 14 and one or more secondary diagnostic parameters to detect worsening heart failure in patient 14. It should be understood, however, that system 10 may, in some embodiments, be implemented as a purely diagnostic device that monitors a primary diagnostic parameter, such as intrathoracic impedance or cardiovascular pressure, and one or more secondary diagnostic parameters.

In the example illustrated in FIG. 2, system 10 includes leads 18, 20, and 22 that include electrodes for monitoring intrathoracic impedance and one or more secondary diagnostic parameters. Leads 18, 20, and 22 may be electrically coupled to a stimulation generator and a sensing module of IMD 16 via connector block 38. In some examples, proximal ends of leads 18, 20, 22 may include electrical contacts that electrically couple to respective electrical contacts within connector block 38. In addition, in some examples, leads 18, 20, 22 may be mechanically coupled to connector block 38 with the aid of set screws, connection pins, or another suitable mechanical coupling mechanism.

Each of the leads 18, 20, 22 includes an elongated insulative lead body, which may carry a number of concentric coiled conductors separated from one another by tubular insulative sheaths. In some cases, each of the leads 18, 20, 22 may include cable conductors. Bipolar electrodes 40 and 42 are located adjacent to a distal end of lead 18. In addition, bipolar electrodes 44 and 46 are located adjacent to a distal end of lead 20 and bipolar electrodes 48 and 50 are located adjacent to a distal end of lead 22.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other embodiments, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

As discussed above, IMD 16 includes one or more housing electrodes, such as housing electrode 34, which may be formed integrally with an outer surface of hermetically-sealed housing 60 of IMD 16 or otherwise coupled to housing 60. In some examples, housing electrode 34 is defined by an uninsulated portion of an outward facing portion of housing 60 of IMD 16. Other division between insulated and uninsulated portions of housing 60 may be employed to define two or more housing electrodes. In some examples, housing electrode 34 comprises substantially all of housing 60. As described in further detail with reference to FIG. 3, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 34, 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 34. Additionally, any of the electrodes 40, 42, 44, 46, 48, 50, 62, 64 and 66 may be used in combination with housing electrode 34 to sense intrathoracic impedance of patient 14.

IMD 16 may process the sensed electrical signals to monitor secondary diagnostic parameters such as AF burden, heart rate during AF, VF burden, heart rate during VF, AT burden, heart rate during AT, VT burden, heart rate during VT, activity level, heart rate variability, night heart rate, difference between day heart rate and night heart rate, heart rate turbulence, heart rate deceleration capacity, or baroreflex sensitivity. IMD 16 may also process the intrathoracic impedance sensed by electrodes 34, 40, 42, 44, 46, 48, 50, 62, 64, or 66 as a primary diagnostic parameter to modify an index of worsening heart failure, as well as to detect respiratory rate, depth, or pattern, which may be secondary diagnostic parameters.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 34 in a unipolar configuration. Furthermore, IMD 16 may deliver cardioversion or defibrillation pulses to heart 12 via any combination of elongated electrodes 62, 64, 66, and housing electrode 34. Electrodes 34, 62, 64, 66 may also be used to deliver cardioversion pulses, e.g., a responsive therapeutic shock, to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, it should be understood that system 10 may be configured to include other types of sensors for monitoring diagnostic parameters. As an example, system 10 may be configured to monitor cardiovascular pressure in patient 14 as the primary diagnostic parameter and include one or more pressure sensors on leads 18, 20, and 22, or on an additional lead coupled to IMD 16 and positioned within or proximate to the cardiovascular system of patient 14, e.g., within RV 28.

System 10 may be similarly configured to also include pressure sensors to monitor the respiratory rate of patient 14. As an additional example, IMD 16 may, in some embodiments, include one or more accelerometers to monitor the activity level of patient 14. The accelerometer may be enclosed in housing 60. In some examples, IMD 16 may include sensors to monitor renal function. In some examples, system 10 may include one or more external sensors to monitor a diagnostic parameter. For example, system 10 may include a scale for monitoring the weight of patient 14. In such an example, IMD 16 and the scale communicate with each other via telemetry or a wired connection.

Moreover, IMD 16 need not be implanted within patient 14 as shown in FIG. 1. For example, IMD 16 may be implanted subcutaneously in patient 14 or may be located outside the body of patient 14. In such examples, IMD 16 may monitor primary and secondary diagnostic parameters and deliver defibrillation pulses and other therapies to heart 12 via percutaneous leads that extend through the skin of patient 14 to a variety of positions within or outside of heart 12.

In addition, in other examples, system 10 may include any suitable number of leads coupled to IMD 16, and each of the leads may extend to any location within or proximate to heart 12 or in the chest of patient 14. For example, other example therapy systems may include three transvenous leads and an additional lead located within or proximate to left atrium 36. As other examples, a therapy system may include a single lead that extends from IMD 16 into right atrium 26 or right ventricle 28, or two leads that extend into a respective one of the right ventricle 28 and right atrium 26.

Figure 3:
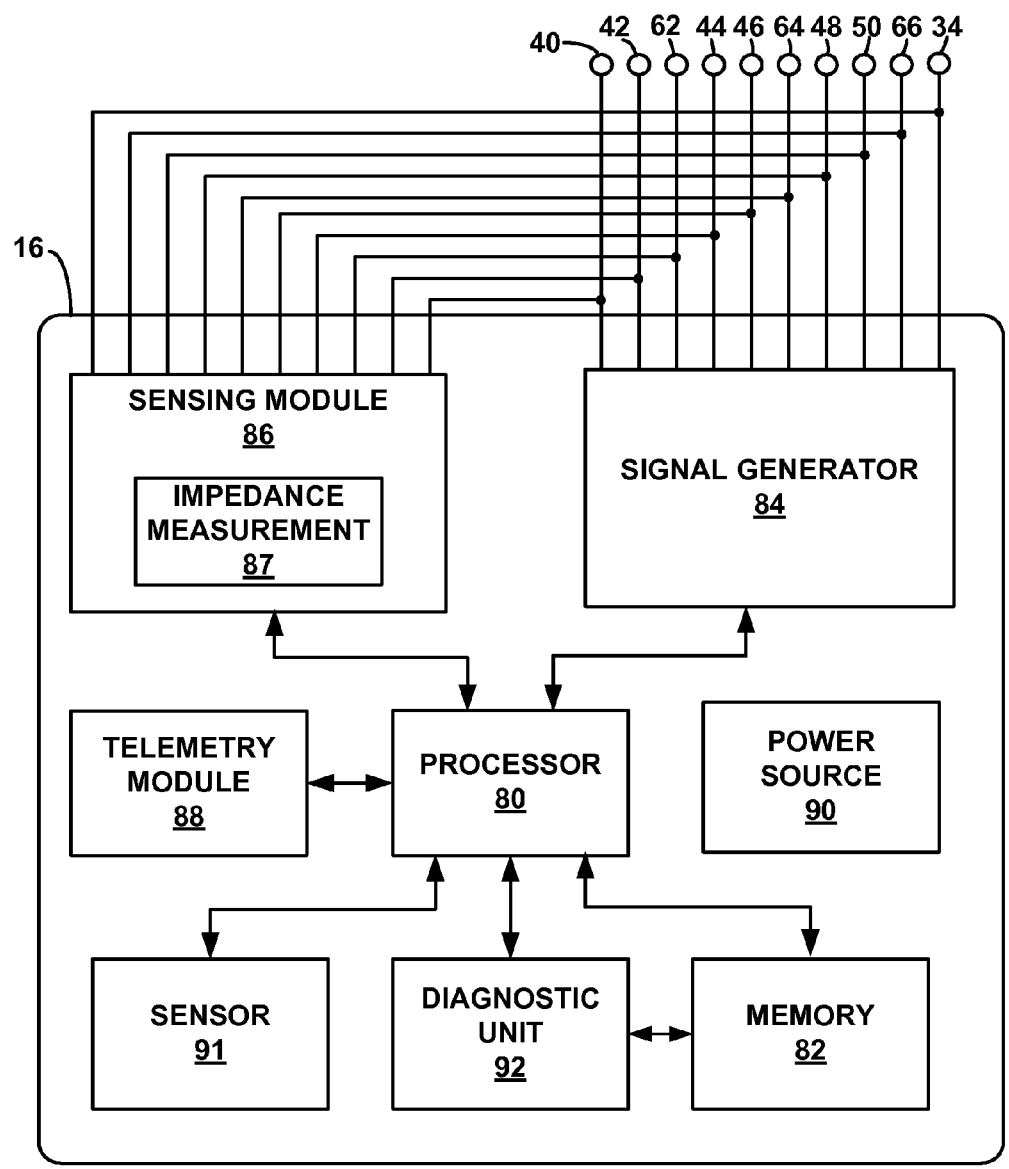
FIG. 3 is a functional block illustrating an example configuration of the IMD shown in FIG. 1.

FIG. 3 is a functional block diagram of one example of IMD 16, which includes a processor 80, memory 82, signal generator 84, electrical sensing module 86, telemetry module 88, power source 90, sensor 91 and diagnostic unit 92. Processor 80 may comprise one or more processors. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 based on a selected one or more of therapy programs, which may be stored in memory 82. Specifically, processor 80 may control signal generator 84 to deliver electrical pulses with the amplitudes, pulse widths, frequency, or electrode polarities specified by the selected one or more therapy programs.

Signal generator 84 is electrically coupled to electrodes 34, 40, 42, 44, 46, 48, 50, 62, 64, and 66, e.g., via conductors of the respective lead 18, 20, 22, or, in the case of housing electrode 34, via an electrical conductor disposed within housing 60 of IMD 16. A switch matrix may also be provided to connect signal generator 84 to one or more of electrodes 34, 40, 42, 44, 46, 48, 50, 62, 64, and 66. Signal generator 84 is configured to generate and deliver electrical stimulation therapy to heart 12.

For example, signal generator 84 may deliver defibrillation shocks to heart 12 via at least two of electrodes 34, 62, 64, 66. Signal generator 84 may also deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals.

Signal generator 84 may include a switch module, and processor 80 may use the switch module to select, e.g., via a data/address bus, which of the available electrodes are used to deliver defibrillation pulses or pacing pulses. The switch module may include a switch array, switch matrix, multiplexer, transistor array, microelectromechanical switches, or any other type of switching device suitable to selectively couple stimulation energy to selected electrodes.

Electrical sensing module 86 monitors signals from at least one of electrodes 34, 40, 42, 44, 46, 48, 50, 62, 64 or 66 in order to monitor electrical activity of heart 12. Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may comprise an amplifier. In response to the signals from processor 80, the switch module within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in right ventricle 28 of heart 12. Another channel may include another R-wave amplifier that receives signals from electrodes 44 and 46, which are used for pacing and sensing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSI- OLOGIC SIGNALS," and is incorporated herein by reference in its entirety. Other amplifiers may also be used. Furthermore, in some examples, one or more of the sensing channels of sensing module 84 may be selectively coupled to housing electrode 34, or elongated electrodes 62, 64, or 66, with or instead of one or more of electrodes 40, 42, 44, 46, 48 or 50, e.g., for unipolar sensing of R-waves or P-waves in any of chambers 26, 28, 36, or 32 of heart 12.

In some examples, sensing module 84 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the patient's heart rhythm by employing any of the numerous signal processing methodologies known in the art.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber that is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, the pulse widths of the pacing pulses, A-V intervals, and V-V intervals for cardiac resynchronization therapy (CRT). As another example, the pacer timing and control module may define a blanking period, and provide signals sensing module 86 to blank one or more channels, e.g., amplifiers, for a period during and after delivery of electrical stimulation to heart 12. As another example, the pacer timing and control module may control intervals for delivery of refractory period stimulation or cardiac potentiation therapy. The durations of these intervals may be determined by processor 80 in response to stored data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves. Stimulation generator 84 may include pacer output circuits that are coupled, e.g., selectively by a switching module, to any combination of electrodes 34, 40, 42, 44, 46, 48, 50, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions, including anti-tachyarrhythmia pacing (ATP).

The value of the count present in the escape interval counters when reset by sensed R-waves and P-waves may be used by processor 80 to measure the durations of R-R intervals, P-P intervals, PR intervals and R-P intervals, which are measurements that may be stored in memory 82. Processor 80 may use the count in the interval counters to detect an arrhythmia event, such as an atrial or ventricular fibrillation or tachycardia.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. are incorporated herein by reference in their entireties. However, other arrhythmia detection methodologies may also be employed by processor 80 in other examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver defibrillation pulses to heart 12, signal generator 84 may include a high voltage charge circuit and a high voltage output circuit. If IMD 16 is configured to generate and deliver pacing pulses to heart 12, signal generator 84 may include a low voltage charge circuit and a low voltage output circuit. In the event that generation of a cardioversion or defibrillation pulse is required, processor 80 may employ the escape interval counter to control timing of such cardioversion and defibrillation pulses, as well as associated refractory periods.

In response to the detection of atrial or ventricular fibrillation or tachyarrhythmia requiring a cardioversion pulse, processor 80 may activate a cardioversion/defibrillation control module, which may, like pacer timing and control module, be a hardware component of processor 80 and/or a firmware or software module executed by one or more hardware components of processor 80. The cardioversion/ defibrillation control module may initiate charging of the high voltage capacitors of the high voltage charge circuit of signal generator 84 under control of a high voltage charging control line.

Processor 80 may monitor the voltage on the high voltage capacitor may be monitored, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by signal generator 84 is controlled by the cardioversion/defibrillation control module of processor 80. Following delivery of the fibrillation or tachycardia therapy, processor 80 may return signal generator 84 to a cardiac pacing function and await the next successive interrupt due to pacing or the occurrence of a sensed atrial or ventricular depolarization.

Signal generator 84 may deliver cardioversion or defibrillation pulses with the aid of an output circuit that determines whether a monophasic or biphasic pulse is delivered, whether housing electrode 34 serves as cathode or anode, and which electrodes are involved in delivery of the cardioversion or defibrillation pulses. Such functionality may be provided by one or more switches or a switching module of signal generator 84.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

As illustrated in FIG. 3, sensing module 86 may include an impedance measurement module 87. Processor 80 may control impedance measurement module 87 to periodically measure an electrical parameter to determine an impedance, such as a intrathoracic impedance. For a intrathoracic impedance measurement, processor 80 may control stimulation generator 84 to deliver an electrical signal between selected electrodes and impedance measurement module 87 to measure a current or voltage amplitude of the signal. Processor 80 may select any combination of electrodes 34, 40, 42, 44, 46, 48, 50, 62, 64, and 66, e.g., by using switch modules in signal generator 84 and sensing module 86. Impedance measurement module 87 includes sample and hold circuitry or other suitable circuitry for measuring resulting current and/or voltage amplitudes. Processor 80 determines an impedance value from the amplitude value(s) received from impedance measurement module 87.

In some examples, processor 80 may perform an impedance measurement by causing signal generator 84 to deliver a voltage pulse between two electrodes and examining resulting current amplitude value measured by impedance measurement module 87. In these examples, signal generator 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12.

In other examples, processor 80 may perform an impedance measurement by causing signal generator 84 to deliver a current pulse across two selected electrodes. Impedance measurement module 87 holds a measured voltage amplitude value. Processor 80 determines an impedance value based upon the amplitude of the current pulse and the amplitude of the resulting voltage that is measured by impedance measurement module 87. IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue.

In certain cases, IMD 16 may measure intrathoracic impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components.

In the illustrated example shown in FIG. 3, IMD 16 includes diagnostic unit 92. Diagnostic unit 92 provides functionality that enables IMD 16 to detect worsening heart failure in patient 14. To avoid confusion, although diagnostic unit 92 is described as performing the various monitoring and detecting techniques proscribed to IMD 16, it should be understood that these techniques may also be performed by processor 80, e.g., that diagnostic unit 92 may be a functional module provided or executed by processor 80. Accordingly, although processor 80 and diagnostic unit 92 are illustrated as separate modules in FIG. 3, processor 80 and diagnostic unit 92 may be incorporated in a single processing unit or equivalent circuitry.

In operation, diagnostic unit 92 monitors a primary diagnostic parameter and one or more secondary diagnostic parameters to detect worsening heart failure in patient 14. Diagnostic unit 92 may operate in accordance with any detection algorithm described in this disclosure. The detection algorithm may be loaded from memory 82 or any other memory. Example detection algorithms specify physiological parameters that are used as the primary and second diagnostic parameters, threshold zone characteristics, and detection rules. As an example, a detection algorithm may specify thransthoracic impedance for the primary diagnostic parameter, AT/AF burden for the secondary diagnostic parameter, the range of index values for the threshold zone, and one or more AT/AF burden conditions. If the detection algorithm provides for multiple secondary diagnostic parameters, such as AT/AF burden and activity level, the detection algorithm specifies the rules used for detecting worsening heart failure based on the AT/AF burden and activity level conditions, i.e., whether one or both of the AT/AF burden and the activity level conditions must be satisfied in order to detect worsening heart failure in patient 14.

In the example illustrated in FIG. 3, diagnostic unit 92 may receive signals or indications from processor 80, sensing module 86 or other sensors 91 to monitor the primary and secondary diagnostic parameters. Thus, IMD 16 may be configured to monitor physiological parameters that are capable of being sensed using any combination of electrodes 34, 40, 42, 44, 46, 48, 50, 62, 64 and 66. For example, IMD 16 may be configured to monitor intrathoracic impedance and/or electrical activity of heart 12, using any combination of electrodes 34, 40, 42, 44, 46, 48, 50, 62, 64 and 66.

Based on the electrical activity of heart 12 as indicated by sensing module 86, diagnostic unit 92 may monitor AF burden, heart rate during AF, VF burden, heart rate during VF, AT burden, heart rate during AT, VT burden, heart rate during VT, heart rate variability, night heart rate difference between day heart rate and night heart rate, heart rate turbulence, heart rate deceleration capacity, or baroreflex sensitivity. As previously described, sensing module 86 monitors signals from a selected combination of electrodes 34, 40, 42, 44, 46, 48, 50, 62, 64, and 66 and processor 80/diagnostic unit 92 may detect atrial or ventricular tachyarrhythmia based on signals or indications from sensing module 86. An AT burden may be determined based on the number and/or duration (individual, average, or collective) of incidents of AT, as well as the ventricular rate during AT. AF, VT and VF burdens may be similar determined. In some examples, AT and AF burdens are combined as an AT/AF burden. VT and VF burdens may likewise be combined, in some examples. Such tachyarrhythmia burdens, as well as heart rate variability and night heart rate, are examples of secondary diagnostic parameters that may be monitored by diagnostic unit 92.

IMD 16 may also be configured, in various examples, to monitor other diagnostic parameters. In some examples, IMD 16 may be configured to include other types of sensors, such as sensor 91 illustrated in FIG. 3, suitable for monitoring other primary and secondary diagnostic parameters, such as one or more pressure sensors for monitoring a cardiovascular pressure in patient 14, one or more accelerometers for monitoring the activity level of patient 14, one or more pressure sensors for monitoring the heart rate variability and night heart rate of patient 14, and/or one or more pressure sensors for monitoring the respiratory rate, depth or pattern of patient 14. In such embodiments, pressure sensors may be carried by leads 18, 20, or 22 or by one or more additional leads coupled to IMD 16. In embodiments in which IMD 16 monitors the activity level of patient 14, one or more accelerometers may be contained within or positioned on the housing of IMD 16, may be carried by one or more of leads 18, 20, and 22 or one or more additional leads, or may be a remote sensor in communication with IMD 16. In addition to fluid accumulation as a primary diagnostic parameter, in some examples, diagnostic unit 92 may monitor respiratory rate, depth or pattern of patient 14 as a secondary diagnostic parameter based on the intrathoracic impedance determined based on signals received from impedance measurement module 87. In some examples, IMD 16 may include sensors, such as chemical, pressure or fluid sensors, for monitoring renal function. Furthermore, in some examples, diagnostic unit 92 may receive signals or information from external sources, such as programmer 24 or an external sensor, such as a scale, and monitor such information or signals as secondary diagnostic parameters. Additionally, diagnostic unit 92 may receive information from processor 80, or may maintain information in memory 82, indicating percentage of CRT pacing as a secondary diagnostic parameter. Diagnostic unit 92 or processor 80 may determine whether or not CRT pacing is delivered based on information from processor 80 of a pacer timing and control module thereof.

If diagnostic unit 92 detects worsening heart failure of patient 14, diagnostic unit 92 may provide an alert to patient 14. Diagnostic unit 92 may include or be coupled to an alert module (not shown) that provides, as examples, an audible or tactile alert to patient 14 of the worsening heart failure. In some examples, diagnostic unit 92 additionally or alternatively provide an indication of worsening heart failure to programmer 24 or another device via telemetry module 88 and/or network, which may provide an alert to a user, such as patient 14 or a clinician.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis.

Figure 4:
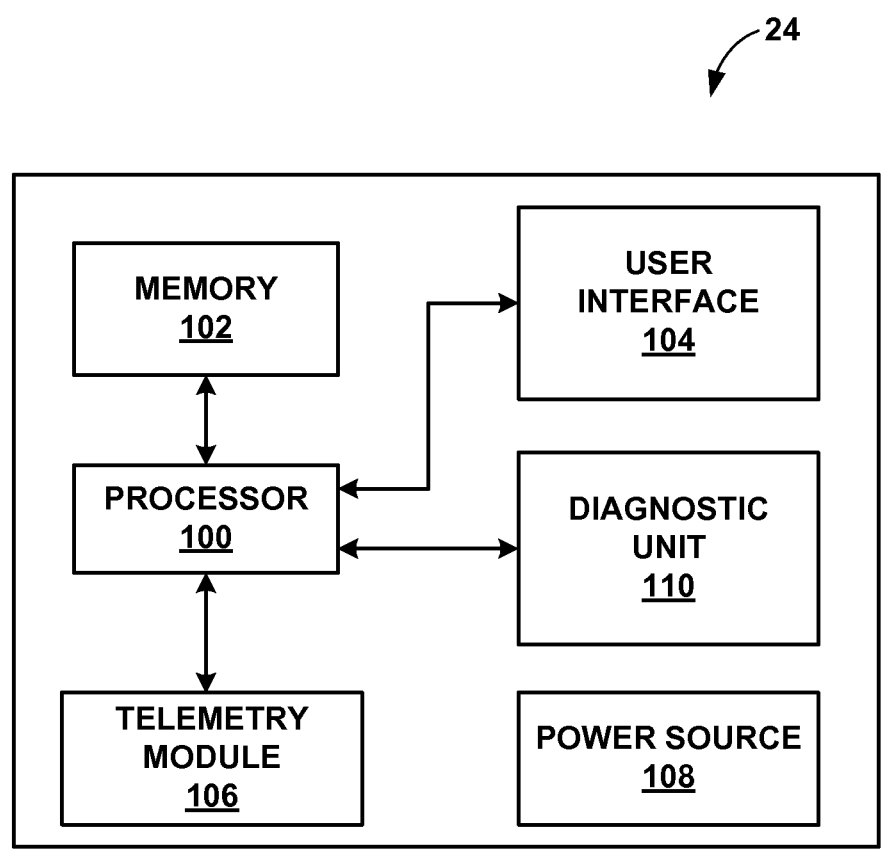
FIG. 4 is a functional block diagram illustrating an example configuration of the programmer shown in FIG. 1.

FIG. 4 is block diagram of an example programmer 24. As shown in FIG. 4, programmer 24 includes processor 100, memory 102, user interface 104, telemetry module 106, and power source 108. In some examples, programmer 24, as illustrated in FIG. 4, includes a diagnostic unit 110. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select worsening heart failure detection algorithms, e.g., select primary and secondary diagnostic parameters from a list of possible diagnostic parameters, select threshold zone characteristics, and select rules for detecting worsening heart failure in patient 14 based on the selected diagnostic parameters and threshold zone. A user may also use programmer 24 to configure other sensing or any therapy provided by IMD 16. The clinician may interact with programmer 24 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Diagnostic unit 110, although illustrated as a separate module in FIG. 4, may be incorporated in a single processing unit with processor 100 or functional module executed or provided by processor 100. Memory 102 may store instructions that cause processor 100 and/or diagnostic unit 110 to provide the functionality ascribed to programmer 24 herein, and information used by processor 100 and/or diagnostic unit 110 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls operation of IMD 16, such as therapy delivery values.

A user, such as a clinician, technician, or patient 14, may interact with programmer 24 via user interface 104. User interface 106 may include display to present graphical user interface to a user, and a keypad or another mechanism for receiving input from a user. In some examples, user interface 106 may include a touch screen display.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 3).

Programmer 24 may also be configured to communicate with another computing device via wireless communication techniques, or direct communication through a wired, e.g., network, connection. Examples of local wireless communication techniques that may be employed to facilitate communication between programmer 24 and another computing device include RF communication based on the 802.11 or Bluetooth specification sets, infrared communication, e.g., based on the IrDA standard.

Power source 108 delivers operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 108 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

In some examples, IMD 16 may detect worsening heart failure using any of the techniques described herein, and provide an indication of worsening heart failure to programmer 24. In such examples, programmer 24 need not include diagnostic module 110. Processor 100 may control user interface 106 to provide an alert of worsening heart failure of patient 14 to the patient, a clinician, or other users. In some examples, processor 100 may provide an alert of worsening heart failure of patient 14 to one or more computing devices via a network. A user may use programmer 24 to retrieve and/or view data regarding primary and secondary diagnostic parameters.

In some examples, programmer 24 includes diagnostic module 110 that receives diagnostic data from IMD 16, or other implanted or external sensors or devices, i.e., data regarding the primary and secondary diagnostic parameters, and processes the received data to detect worsening heart failure in patient 14. In this manner, diagnostic unit 110 may perform substantially the same functionality as described with respect to diagnostic unit 92 in FIG. 3. IMD 16 may not need to include diagnostic unit 92 in examples in which programmer 24 includes diagnostic unit 110. Diagnostic unit 110 may include an alert module that provides an alert to patient 14 or a clinician via user interface 104 when worsening heart failure is detected in patient 14, and/or provides a notification to one or more computing devices via a network.

Alerts provided via user interface 104 may include a silent, audible, visual, or tactile alert. For example, user interface 104 may emit a beeping sound, display a text prompt, cause various buttons or screens to flash, or vibrate to alert patient 14 or another user that a heart failure decompensation event may be likely to occur. Patient 14 may then seek medical attention, e.g., check in to a hospital or clinic, to receive appropriate treatment, or the other user may instruct patient 14 to do so.

Although illustrated and described in the context of examples in which programmer 24 is able to program the functionality of IMD 16, in other examples a device capable of communicating with IMD 16 and providing functionality attributed to programmer 24 herein need not be capable of programming the functionality of the IMD. For example, an external home or patient monitor may communicate with IMD 16 for any of the purposes described herein, but need not independently be capable of programming the functionality of the IMD. Such as a device may be capable of communicating with other computing devices via a network, as discussed in greater detail below.

The components of and functionality provided by a diagnostic unit for detecting worsening heart failure are described in greater detail below with respect to diagnostic unit 92 of IMD 16. However, it is understood that any diagnostic unit provided in any device, such as diagnostic unit 110 of programmer 24, may include the same or similar components and provide the same or similar functionality.

Figure 5:
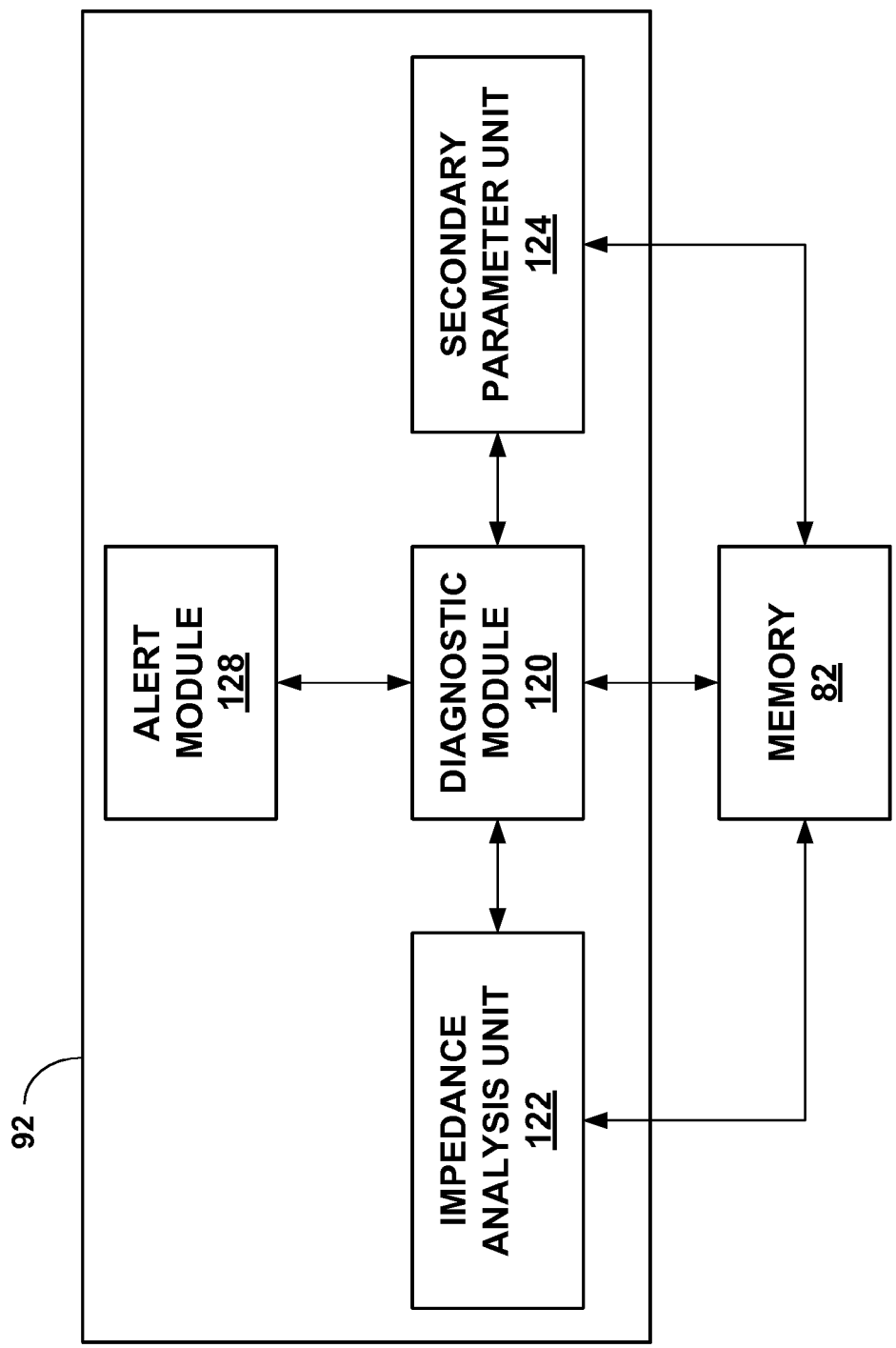
FIG. 5 is a functional block diagram illustrating an example configuration of a diagnostic unit shown in FIG. 3 and FIG. 4.

FIG. 5 is a block diagram of an example configuration of diagnostic unit 92. As shown in FIG. 5, diagnostic unit 92 includes multiple components including diagnostic module 120, impedance analysis unit 122, and secondary parameter unit 124, and alert module 128. Because either IMD 16 or programmer 24 may be configured to include a diagnostic unit, modules 120, 122, 124, and 128 (and their sub-modules described below with reference to FIGS. 6-8) may be implemented in one or more processors, such as processor 80 of IMD 16 or processor 100 of programmer 24. The modules of diagnostic unit 92 (and their sub-modules described below with reference to FIGS. 6-8) may be embodied as one or more hardware modules, software modules, firmware modules, or any combination thereof. As illustrated in FIG. 5, the modules and sub-modules of diagnostic unit 92 may have access to memory for buffering or storing any of the values discussed with reference to FIGS. 5-8, e.g., at locations accessible by and known to these modules.

Generally, diagnostic module 120 processes data received from impedance analysis unit 122 and secondary diagnostic parameter unit 124 to detect worsening heart failure in patient 14. Accordingly, impedance analysis unit 122 and secondary diagnostic parameter unit 124 may operate in a coordinated manner with diagnostic module 120. In one example embodiment, diagnostic module 120 may retrieve timing information from memory 126. The timing information may provide periodic intervals for monitoring primary and secondary diagnostic parameters and detecting worsening heart failure based on the parameters. Accordingly, diagnostic module 120 may invoke impedance analysis unit 122 and secondary parameter unit 124 based on the timing information. Alternatively, diagnostic module 120 may load the timing information into impedance analysis unit 122 and secondary parameter unit 124, and units 122 and 124 may monitor corresponding parameters according to the timing information. In either case, diagnostic module 120, impedance analysis unit 122, and secondary parameter unit 124 operate together to periodically monitor primary and secondary diagnostic parameters of patient 14 and detect worsening heart failure in patient 14 based on the diagnostic parameters.

Impedance analysis unit 122 monitors the intrathoracic impedance of patient 14 as previously described with respect to FIG. 3. That is, impedance analysis unit 122 may receive intrathoracic impedance values measured using the techniques described above with respect to FIG. 3. Although impedance analysis unit 122 is illustrated in FIG. 5, it should be understood that impedance analysis unit 122 is one example of various primary diagnostic parameter analysis units that may be utilized. In other example embodiments, diagnostic unit 92 may be configured to include, in place of impedance analysis unit 122, a pressure analysis unit that monitors one or more cardiovascular pressures of patient 14.

Secondary parameter unit 124 may monitor one or more secondary diagnostic parameters and output corresponding data to diagnostic module 120. For example, secondary diagnostic unit 124 may obtain measured values, process the measured values to detect worsening heart failure, and output secondary parameter data that indicates whether worsening heart failure is detected in patient 14. With respect to FIG. 3, secondary diagnostic unit 124 may monitor secondary diagnostic parameters, e.g., AT/AF or VT burden, activity level, night heart, difference between day heart rate and night heart rate, heart rate turbulence, heart rate deceleration capacity, percentage of CRT pacing, heart rate variability, respiratory rate, and other parameters that indicate worsening heart failure, based on signals or indications received from sensing module 86.

Diagnostic module 120 processes data received from impedance analysis unit 122 and secondary parameter unit 124 according to a detection technique or algorithm. The detection technique may be loaded from memory 82. Memory 82 may store a plurality of detection techniques. Each detection technique may specify primary and secondary diagnostic parameters, rules regarding determining a value of an index of worsening heart failure based on the primary diagnostic parameter, rules regarding the threshold zone, and rules for detecting worsening heart failure based on the index, threshold zone, and secondary diagnostic parameter.

The rules regarding the threshold zone may specify the range of values for the threshold zone. If the threshold zone dynamically changes over time, the rules may also control how the threshold zone changes as a function of time or as a function of knowledge, such as knowledge of the condition of patient 14. The rules for detecting worsening heart failure may specify threshold values associated with the primary and secondary diagnostic parameters. The threshold values correspond to a condition that must be satisfied to detect worsening heart failure. As an example, when multiple secondary diagnostic parameters are used one detection technique may require that at least one secondary diagnostic parameter exceed a corresponding threshold value, and another detection technique may require that each of the secondary diagnostic parameters exceed a corresponding threshold value.

Diagnostic module 120 invokes alert module 128 in response to detecting worsening heart failure in patient 14. Alert module 128 provides an alert to patient 14 by, for example, providing an audible, visual, or tactile alert. Alert module 128 may cause IMD 16 to emit a beeping a sound or vibrate. In some examples, alert module 128 may provide an alert by communicating with an external device, such as programmer 24. In response to the communication from alert module 128, programmer 24 may emit a beeping sound, display a text prompt, vibrate, or cause buttons and/or screens of programmer 24 to flash. Similarly, if the alert module is implemented in programmer 24, alert module 128 may cause programmer 24 to send a telemetry signal to IMD 16 that causes IMD 16 to generate the alert.

Figure 6:
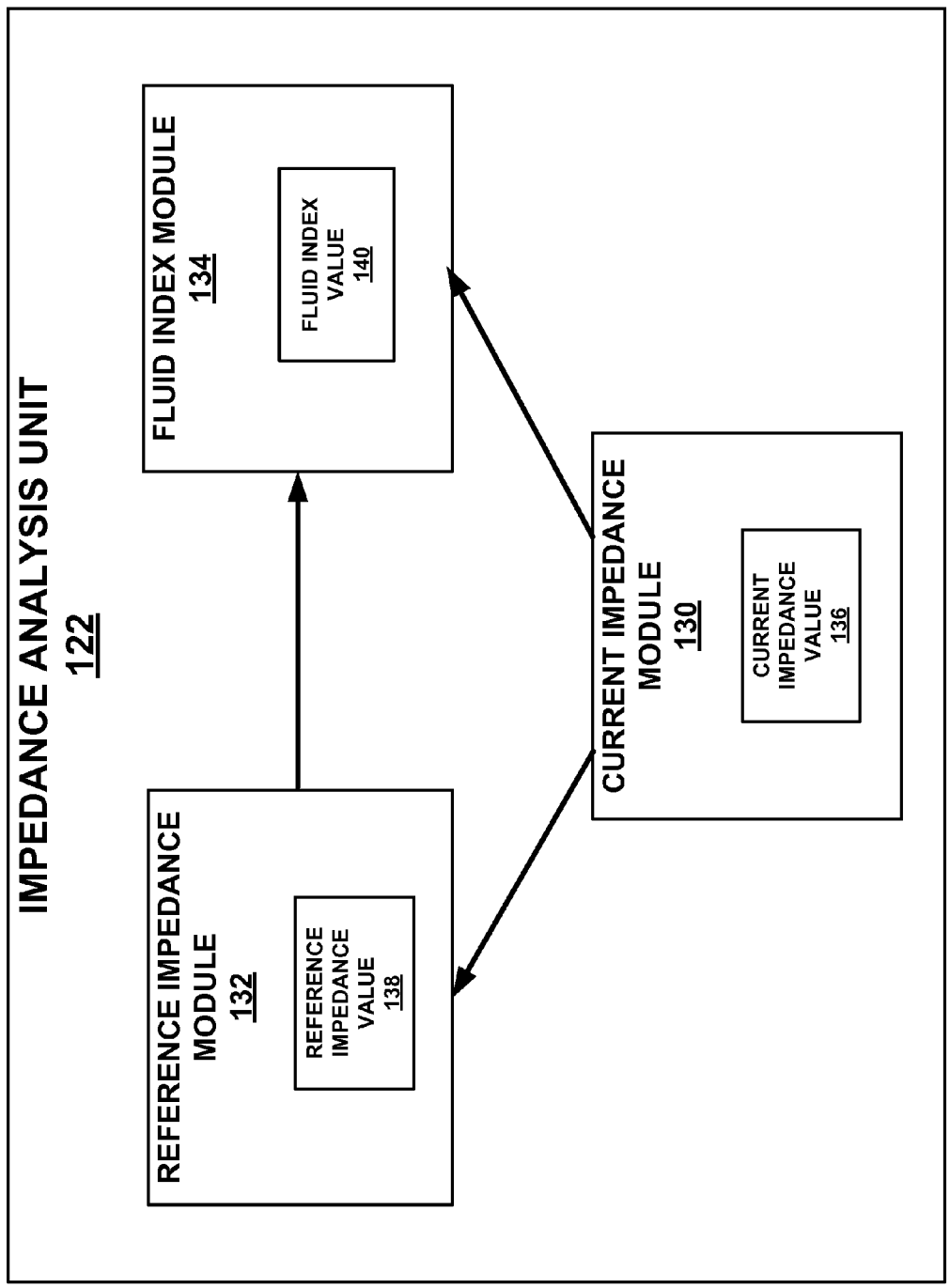
FIG. 6 is functional block diagram illustrating an example configuration of an impedance analysis unit shown in FIG. 5.

FIG. 6 is a block diagram of an example configuration of impedance analysis unit 122. As shown in FIG. 6, impedance analysis unit 122 includes a current impedance module 130, a reference impedance module 132 and a fluid index module 134. In general, impedance analysis unit 122 periodically receives (or accesses) intrathoracic impedance values measured as described above, and determines, e.g., updates, a value of a fluid index 138 based on the impedance values. Impedance analysis unit 122 provides the current fluid index value 140 to diagnostic module 120 (FIG. 5) for comparison to the threshold zone.

The fluid index may reflect a level of fluid accumulation, e.g., pulmonary edema. The fluid index is one example of an index that indicates worsening heart failure. Other examples include indices or metrics of increased ventricular filling pressures or other morbidities associated with worsening heart failure experienced by a patient. In general, any parameter described herein as indicating worsening heart failure may be a primary diagnostic parameter, and an index that indicates worsening heart failure may be any index that is incremented to indicate a trend in the primary diagnostic parameter (that reflects worsening heart failure).

Impedance measurement module 87 and/or processor 80 (FIG. 3) may measure impedance values on an hourly basis, daily basis, weekly basis, or other periodic interval. In one example embodiment, impedance measurement module 87 may measure impedance values during a particular portion of a day. As an example, impedance measurement module 87 may measure impedance values every twenty minutes during the afternoon. In some examples, current impedance module 130 determines a current impedance value 136 as an average or median of a plurality of such measured values, e.g., a daily average. Current impedance module 130 may utilize a buffer to store a plurality of measured impedance values to determine current impedance value 136. In other examples, current impedance value 136 may be a single, most recently measured impedance value.

Reference impedance module 132 generates a reference impedance value 138 based on the current impedance values 136 determined by current impedance module 130 over time. For example, reference impedance module 132 may compare current impedance value 136 to a previous current impedance value, and determine a new reference impedance value 138 based on the comparison. Reference impedance module 132 may generate a new reference impedance value 138 based on the prior reference impedance value.

For example, when the current impedance value 136 is greater than the previous impedance value, reference impedance module 132 may generate a new reference impedance value 138 by adding a predetermined value to the previous reference impedance value. Similarly, reference impedance module 132 may generate a new reference impedance value 138 by subtracting a predetermined value from the prior reference impedance value if the current impedance value is less than a previous impedance value. In other words, reference impedance module 132 may generate reference impedance values 138 by incrementing or decrementing the reference impedance value based on the comparison of the current impedance value 136 to the previous impedance value. In other examples, reference impedance module 132 may determine reference impedance value as an average or median, e.g., over a window, of previous impedance values 136. Reference impedance module 132 may utilize buffers or other memory to store previous impedance values 136.

Fluid index value 140 represents decreasing intrathoracic impedance in patient 14, and is accumulated over time to detect worsening heart failure. Fluid index module 134 determines, e.g., changes, fluid index value 140 based on a comparison of current impedance value 136 to reference impedance value 138. For example, fluid index module 134 may increment fluid index value 134 by the difference between current impedance value 136 and reference impedance value 138 when the current impedance value is less than the reference impedance value for a particular measurement interval. Fluid index module 134 may decrement fluid index value 140 when the current impedance value is greater than the reference impedance value for a particular measurement interval. The decrement may be by the difference between current impedance value 136 and reference impedance value 138, by or to a predetermined value, or to a value of zero. In some examples, impedance analysis unit may determine current impedance value 136, reference impedance value 138 and fluid index value 140 using any of the techniques described in a commonly-assigned and co-pending U.S. application by Sarkar et al., entitled "DETECTING WORSENING HEART FAILURE BASED ON IMPEDANCE MEASUREMENTS," filed on even date herewith, and/or commonly-assigned U.S. application Ser. No. 10/727,008 by Stadler et al., entitled "METHOD AND APPARATUS FOR DETECTING CHANGE IN INTRATHORACIC IMPEDANCE," filed on Dec. 3, 2003. Each of these preceding applications by Sarkar et al. and Stadler et al. are incorporated herein by reference in their entirety. As mentioned above, impedance analysis unit 122 provides the fluid index value 140 to diagnostic module 120 (FIG. 5) for comparison to the threshold zone in the described in greater detail below. Diagnostic module 120 compares fluid index value 140 to the threshold zone to determine whether to provide an alert to patient 14, continue monitoring patient 14, or examine the secondary diagnostic parameter.

Figure 7:
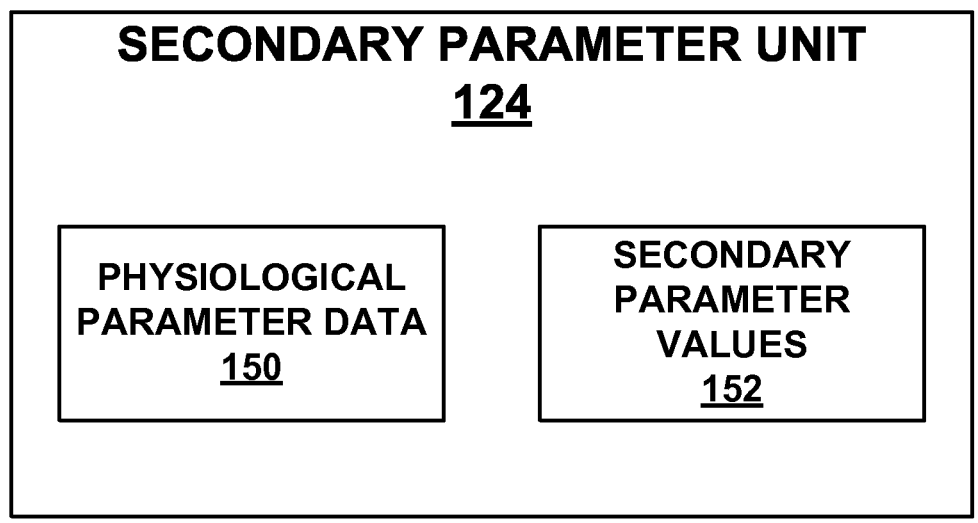
FIG. 7 is a functional block diagram illustrating an example of the functionality of a secondary diagnostic parameter unit shown in FIG. 5.

FIG. 7 is a block diagram illustrating the functionality of secondary parameter unit 124. In general, secondary parameter unit 124 receives physiological parameter or therapy data 150, and determines secondary parameter values 152 based on the physiological parameter or therapy data. Secondary parameter values 152 may be used by diagnostic module 120 (FIG. 5) to detect worsening heart failure in patient 14.

Although secondary parameter unit 124 is described generally with respect to FIG. 7, i.e., described without reference to a specific secondary diagnostic parameter, it should be understood that secondary parameter unit 124 may be used to determine secondary parameter values 152 for any of the secondary diagnostic parameters discussed above. Furthermore, second parameter unit 124 may determine secondary parameter values 152 for a plurality of secondary diagnostic parameters or, alternatively, diagnostic unit 92 may include a secondary parameter unit 124 for each secondary diagnostic parameter used to detect worsening heart failure in patient 14.

For example, secondary parameter unit 124 or multiple secondary parameter units may generate secondary parameter values 152 for AF burden, AT burden, AT/AF burden, VT burden, patient activity, night heart rate, difference between day heart rate and night heart rate, heart rate turbulence, heart rate deceleration capacity, baroreflex sensitivity, percentage of CRT pacing, heart rate variability, respiration rate, respiration depth, respiration pattern, renal function, patient weight, or patient history. Secondary parameter unit 124 may receive physiological parameter data 150 from one or more of electrical sensing module 86, implanted or external sensors 91, processor 80, or programmer 24 to determine the secondary parameter values 152, e.g., to process data 150 such that is in a form that may be indicative of worsening heart failure. Physiological parameter data 150 may include, as examples, heart rate, indications of the number and duration of AF, AT, or VT episodes, as well as the ventricular rate during such episodes, or digitized intrathoracic impedance signals for determining respiration rate, depth or pattern. In some examples, secondary parameter values 152 may include variable values, such as count variables that are updated, i.e., incremented or decremented or set to a predetermined value, based on received physiological parameter data 150.

Figure 8:
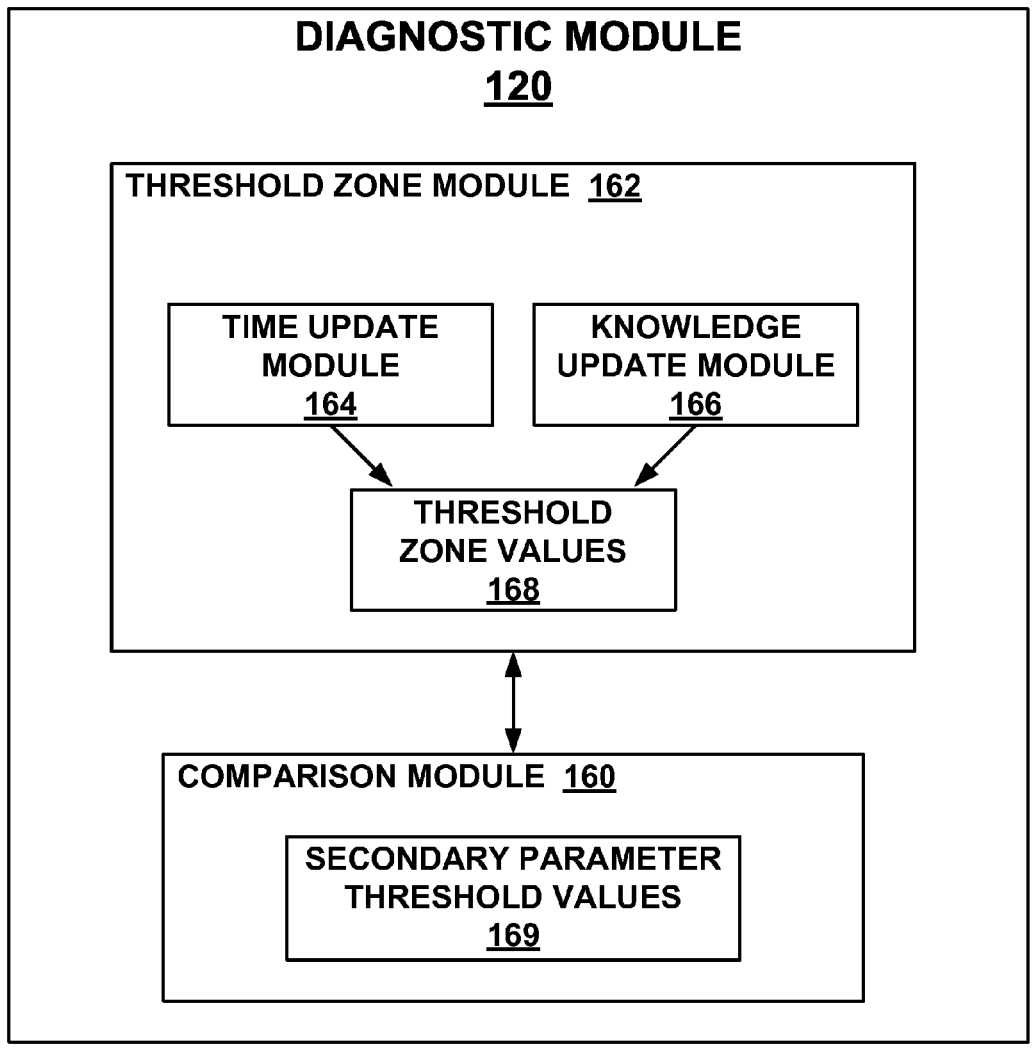
FIG. 8 is a functional block diagram illustrating an example configuration of a diagnostic module shown in FIG. 5.

FIG. 8 is a block diagram of an example configuration of diagnostic module 120. As shown in FIG. 8, diagnostic module 120 includes comparison module 160, threshold zone module 162, time update module 164, knowledge update module 166, threshold zone values 168, and secondary parameter threshold values 169. Generally, comparison module 160 detects worsening heart failure in patient 14 by comparing primary diagnostic parameter values, e.g., fluid index values 140 received from impedance analysis unit 122 (FIG. 6), to values retrieved from threshold zone module 162, and secondary parameter values 152 received from secondary parameter unit 124 (FIG. 7) to secondary parameter threshold values 169. Comparison module 160 activates alert module 128 (FIG. 5) in response to detecting worsening heart failure.

Threshold zone module 162 stores values in threshold zone values 168 that may be variable values and may be output to comparison module 160. The variable values in threshold zone values 168 define the threshold zone and may include threshold values, THRESHOLD_HIGH and THRESHOLD_LOW. In other words, THRESHOLD_HIGH and THRESHOLD_LOW define a range of values that is the threshold zone.

Time update module 164 and knowledge update module 166 may update the threshold values in threshold zone values 168. As an example, time update module 164 may automatically update the threshold values as a function of time to, for example, increase or decrease the size of the threshold zone as time lapses. Time update module 164 may also automatically update the threshold values such that the threshold zone is defined differently over predetermined intervals of time. As another example, knowledge update module 166 may update the threshold values in threshold zone values 168 based on input received from an authorized user of programmer 24. In this way, the size and range of the threshold zone may be manually controlled and adapted based on the symptoms of patient 14. Furthermore, in some examples, knowledge update module 166 may automatically update the threshold values of threshold zones values 168 based on, for example, changes in patient condition observed via one or more of the monitored diagnostic parameters, or indications of efficacy of the diagnostic module 120 in identifying worsening heart failure.

Initially, comparison module 160 compares fluid index value 140, which is determined based on the primary diagnostic parameter, e.g., intrathoracic impedance, as described above to threshold zone values 168. When the fluid index value is outside the range of the threshold zone values 168, i.e. greater than THRESHOLD_HIGH and less than THRESHOLD_LOW, the primary diagnostic parameter value is conclusive. That is, if the fluid index value is greater than THRESHOLD_HIGH, then comparison module 160 activates alert module 128. If, on the other hand, fluid index value 140 is less than THRESHOLD_LOW, IMD 16 continues to monitor patient 14.

However, when fluid index value 140 is within the range of the threshold zone values 138, the primary diagnostic parameter is considered "inconclusive" and comparison module 160 compares one or more secondary diagnostic parameter values 152 to the corresponding secondary parameter threshold values 169. Comparison module 160 detects worsening heart failure in patient 14 based on these comparisons. More specifically, comparison module 160 detects worsening heart failure based on the comparisons in accordance with the particular detection technique.

As previously described, a detection technique specifies the secondary diagnostic parameters, threshold values for comparison to the parameter values, and a condition. Comparison module 160 detects worsening heart failure and invokes alert module 128 (FIG. 5) when the condition is satisfied. As an example, the condition may be satisfied when a secondary diagnostic parameter value 152 exceeds the corresponding secondary diagnostic parameter threshold value 169. However, in an example using multiple secondary diagnostic parameters, different detection techniques specify different conditions, such as a condition that all parameter values exceed corresponding threshold values or, a condition that at least one parameter value exceeds the corresponding threshold value.

Figure 9:
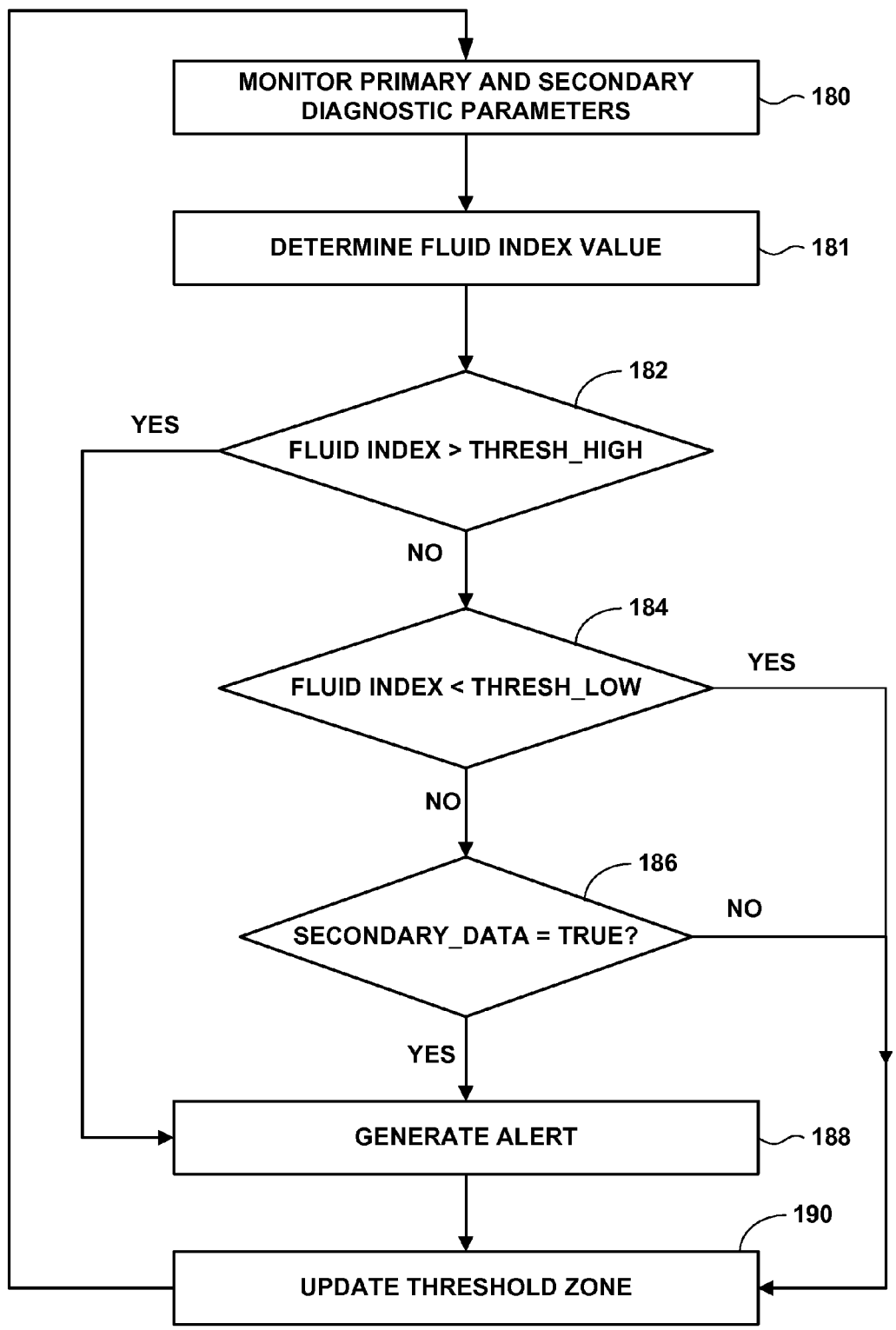
FIG. 9 is a flow diagram illustrating an example method that may be performed by the IMD or programmer shown in FIG. 1 to detect worsening heart failure in a patient.

FIG. 9 is a flow diagram illustrating an example method for detecting worsening heart failure in patient 14. The method may be performed entirely by IMD 16 or by a combination of IMD 16 and programmer 24. When the method is performed by IMD 16 and programmer 24, the steps for monitoring primary and secondary diagnostic parameters, i.e., measuring the primary and secondary diagnostic parameters, may be performed by IMD 16 and the steps for detecting worsening heart failure in patient 14 based on the primary and secondary diagnostic parameters may be performed by programmer 24. In such examples, IMD 16 transmits parameter information to programmer 24 via wireless signals as previously described in this disclosure. For purposes of illustration only, it will be assumed in the subsequent description that IMD 16 performs the method illustrated in FIG. 9. Additionally, the method will be described with respect to diagnostic unit 92 (FIG. 5) and diagnostic module 120 (FIG. 6), but may be performed by any diagnostic unit(s) in any one or more devices.

In the example shown in FIG. 9, IMD 16 monitors primary and secondary diagnostic parameters (180). Based on the primary diagnostic parameter, IMD 16 determines a fluid index value 140 (181). In one example, IMD 16 may periodically measure intrathoracic impedance, and an impedance analysis unit 122 may determine the fluid index value in the manner described above.

Diagnostic module 120 receives the fluid index value 140 value from impedance analysis unit 122 and compares it to a higher threshold value, THRESH_HIGH (182). In particular, comparison module 160 compares the fluid index value 140 to the high threshold value stored in threshold zone values 168. If the fluid index value is greater than the high threshold value ("YES" branch of step 182), then alert module 128 of diagnostic unit 92 generates an alert (190) that indicates worsening heart failure to patient 14. If, however, the fluid index value 140 is less than the high threshold value ("NO" branch of step 182), then diagnostic module 120 compares the fluid index value to a lower threshold value, THRESH_LOW (184). In particular, comparison module 160 may compare fluid index value 140 to the low threshold value stored in threshold zone values 168.

When fluid index value 140 is less than the low threshold value, then IMD 16 may update the threshold zone (192). As previously described, the threshold zone may be updated, i.e., the size and range of the threshold zone may change, as a function of time or based on knowledge of the condition of patient 14. Time update module 164 and knowledge update module 166 of threshold zone module 162 (FIG. 8) may update the threshold zone by updating the higher and lower threshold values stored in threshold zone values 168. Threshold zone module 162 may update threshold zone values 168 periodically, and such updating need not occur after each comparison of fluid index value 140 to the threshold zone values. In some embodiments, the threshold zone is constant and not updated. Whether or not the threshold zone is updated, IMD 16 may continue to monitor the primary and secondary diagnostic parameters (180).

When fluid index value 140 is within the threshold zone, e.g., greater than the lower threshold value and less than the higher threshold value, or between the threshold values ("NO" branch of step 184), diagnostic module 120 determines whether the secondary diagnostic parameter(s). That is, diagnostic module 120 looks to the secondary diagnostic parameters for determining whether the patient is experiencing worsening heart failure when fluid index value 140 is within the threshold zone.

As discussed above, secondary parameter unit 124 may monitor one or more secondary diagnostic parameters to determine secondary diagnostic parameter values, and comparison module 160 of diagnostic module 120 may compare the values to corresponding threshold values to detect worsening heart failure in patient 14. As will be described in greater detail in FIGS. 11-14, comparison module 160 generates secondary parameter data, SECONDARY_DATA, based on the comparison. The secondary parameter data may be a Boolean variable that is set to a true value to indicate worsening heart failure, or a false value if the secondary diagnostic parameter does not indicate worsening heart failure.

Diagnostic module 120 examines the secondary diagnostic parameter data to detect worsening heart failure in patient 14 (186). When the secondary parameter data value is equal to a true value ("YES" branch of step 188), the secondary diagnostic parameter corroborates the primary diagnostic parameter and alert module 128 generates an alert (190) to indicate worsening heart failure to patient 14. On the other hand, when the secondary parameter value is not equal to a true value ("NO" branch of step 188), i.e., equal to a false value, IMD 16 may update the threshold zone (192) and/or continue to monitor the primary and secondary diagnostic parameters (180).

The method shown in FIG. 9 may be performed periodically. That is, the method may be repeated recursively over periodic intervals. For example, the method may repeat once per day, once every hour, once every several hours, once an hour for a sub-period of several hours every day, and the like.

Figure 10:
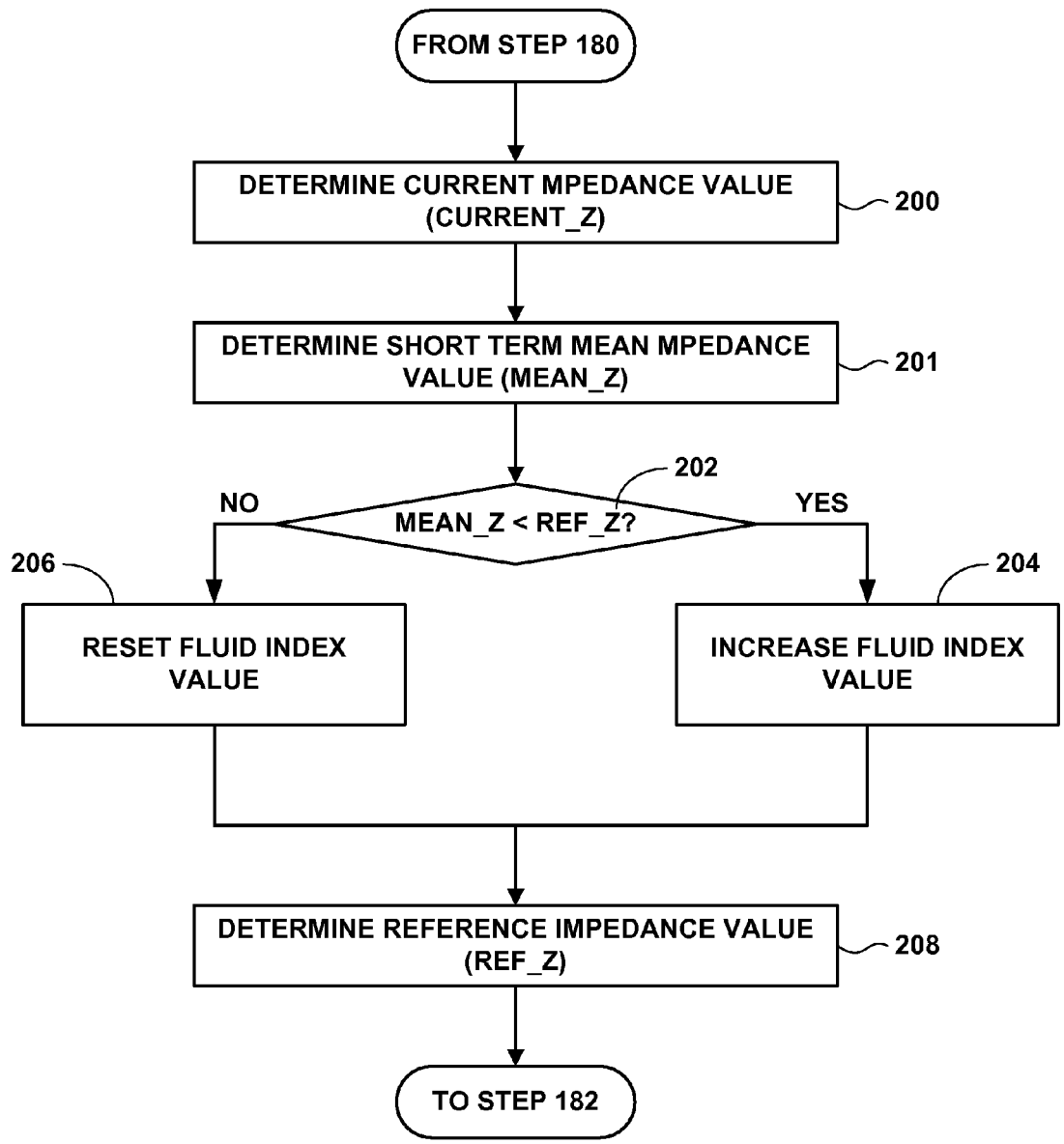
FIG. 10 is a flow diagram illustrating an example method for monitoring a primary diagnostic parameter.

FIG. 10 is a flow diagram illustrating an example method for measuring intrathoracic impedance and determining a fluid index value 140 in patient 14. In particular, the method illustrated in FIG. 10 is described with respect to impedance analysis unit 122 and fluid index module 134 of FIG. 6. Initially, impedance analysis unit 122 determines a current impedance value, CURRENT_Z, based on one or more measured impedance values received from impedance measurement module 87 and/or processor 80 (200). The measured impedance values may be collected at regular intervals throughout the day or during a particular portion of the day. In one example embodiment, impedance analysis unit 122 may determine the current impedance value as the average of impedance values measured every 20 minutes from the hours of 12 p.m. to 5 p.m. during one day. Impedance analysis unit 122 then determines a short term mean impedance value (MEAN_Z) (201). The short term mean may be the mean or weighted mean of the CURRENT_Zs from a plurality of days, e.g., the last three days. To determine the current and mean impedances, impedance analysis unit 122 may employ the techniques described in U.S. application Ser. No. 10/727,008 by Stadler et al., entitled "METHOD AND APPARATUS FOR DETECTING CHANGE IN INTRATHORACIC IMPEDANCE," filed on Dec. 3, 2003, and incorporated herein by reference in its entirety.

Fluid index module 134 compares the mean impedance value to a reference impedance value (202). When the mean impedance value is less than the reference impedance value ("YES" branch of step 202), fluid index module 134 increases fluid index value 140 (204). As previously described, fluid index module 134 may increase the fluid index value by adding the difference between the current impedance value and the reference impedance value to the previous fluid index value. In this way, the fluid index value accumulates over time while the mean impedance value is less than the reference impedance value. However, when the mean impedance value is greater than or equal to the reference impedance value ("NO" branch of step 202), fluid index module 134 resets the fluid index value 140, e.g., to zero (206). In some examples, fluid index module 134 may alternatively decrease fluid index 140 by the difference between the current and reference impedances, by a fixed or predetermined amount, or to a fixed or predetermined value.

In either case, reference impedance module 132 also determines the reference impedance value 138 (REF_Z) for the next iteration of the method based on the mean impedance value (208). For example, reference impedance module 132 may increment reference impedance value 138 by a fixed amount if the mean impedance value 136 is greater than the reference impedance value 138. Reference impedance module 132 may decrement reference impedance value 138 by the same or a different fixed amount if the mean impedance value 136 is less than the reference impedance value 138. In other examples, reference impedance module 132 may update a running average or median (e.g., over a window) based on the current impedance value 136.

FIGS. 11-15 are flow diagrams illustrating example methods for monitoring secondary diagnostic parameters to determine whether a patient is experiencing worsening heart failure. In particular, the flow diagrams illustrated in FIGS. 11-15 are described with respect to secondary parameter unit 124 shown in FIG. 7 and diagnostic unit 120 of FIG. 8.

Figure 11:
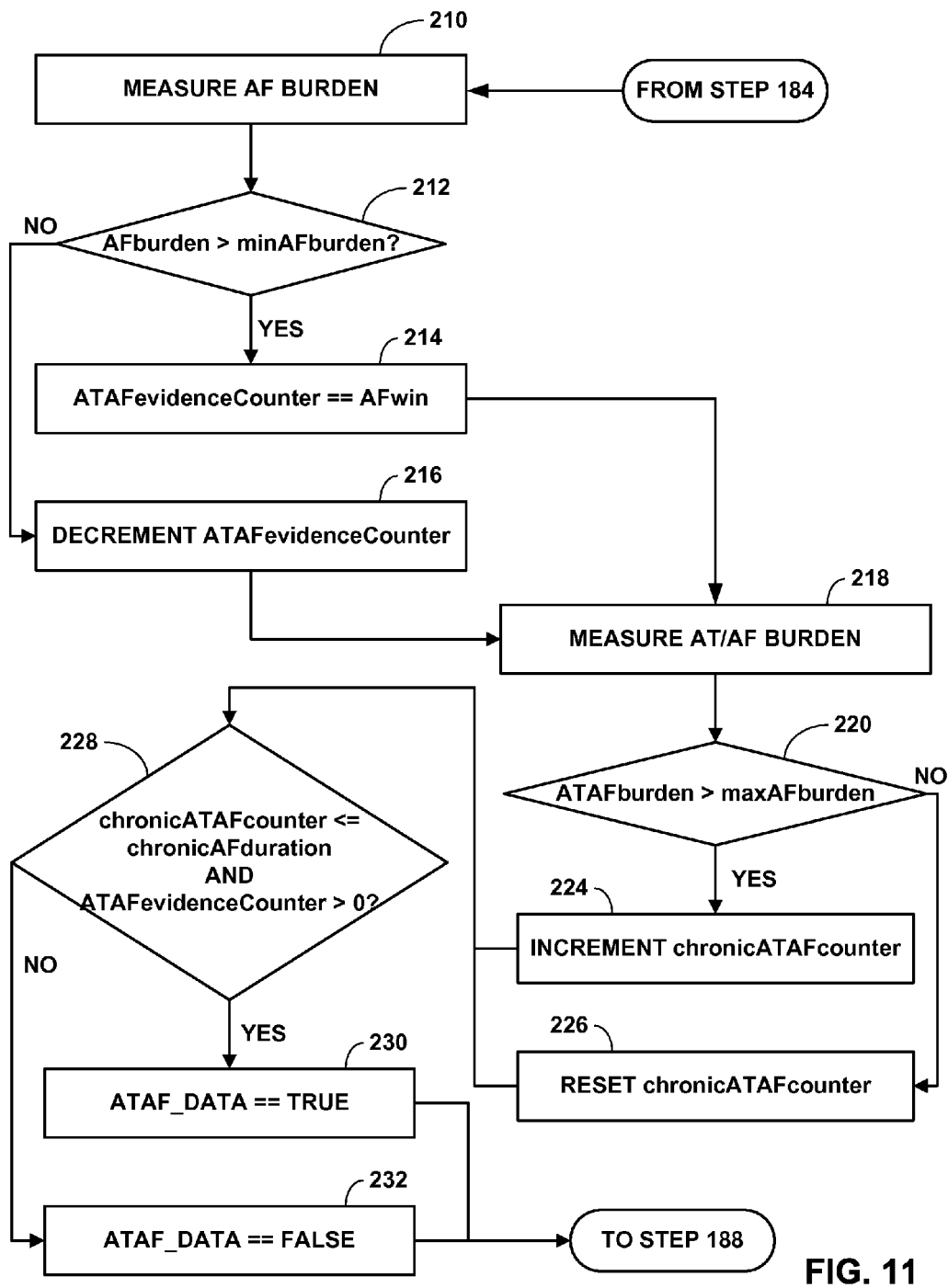
FIGS. 11-15 are flow diagrams illustrating example methods for monitoring secondary diagnostic parameters.

FIG. 11 is a flow diagram illustrating an example method for determining whether a patient is experiencing worsening heart failure based on atrial tachycardia and atrial fibrillation in patient 14. Initially, secondary parameter unit 124 measures an AF burden of patient 14 (210). For example, secondary parameter unit 124 may determine an AF burden value based on the number and/or duration, e.g., average or cumulative duration, of AF episodes experienced by patient 14, as well as the ventricular rate, e.g. average ventricular rate during the episodes.

Next, comparison module 160 compares the measured AF burden value (AFburden) to a corresponding minimum threshold value 212 (minAFburden). If the AF burden value is greater than the minimum threshold value ("YES" branch of step 212), comparison module 160 sets the value of a count variable, ATAFevidenceCounter equal to a predetermined value, AFwin (214). If, however, the AF burden value is less than or equal to the minimum threshold value ("NO" branch of step 212), comparison module 160 decrements the count variable (216). The value of the count variable is generally not decremented lower than zero.

Secondary parameter unit 124 may also measure an AT/AF burden of patient 14 (218). For example, secondary parameter unit 124 may determine an AT/AF burden value based on the AF burden value and an AT burden value, e.g., the sum of these values. The AT burden value may be determined based on the number and/or duration, e.g., average or cumulative duration, of AT episodes experienced by patient 14, as well as the ventricular rate, e.g. average ventricular rate during the episodes.

Comparison module 160 compares the AT/AF burden value (ATAFburden) to a corresponding maximum threshold value (maxAFburden) (220). When the AT/AF value is greater than the maximum threshold value ("YES" branch of step 220), comparison module 160 increments a count variable, chronicATAFcounter (224). However, when the AT/AF value is not greater than the maximum threshold value ("NO" branch of step 220), comparison module 160 resets the count variable (226). In some examples, comparison module 160 may additionally consider the ventricular rate during AT/AF, e.g., determine whether the AT/AF burden was greater than a threshold number of hours and the ventricular rate during the AT/AF was greater than a threshold rate, to determine whether to increment the chronic AT/AF counter. In other examples, only AT/AF associated with a threshold ventricular rate may be counted as AT/AF burden that is compared to the maxAFburden threshold. In these ways, the devices according to this disclosure may consider whether AT/AF was conducted to the ventricles.

Diagnostic module 120 compares the count variable, chronicATAFcounter, to a threshold value, chronicAFduration, and the count variable, ATAFevidenceCounter, to a threshold value, zero (228). In this way, this comparison is used to determine whether the AT/AF burden satisfies corresponding conditions that corroborate worsening heart failure in patient 14. In some examples, when both conditions are satisfied ("YES" branch of step 228), comparison module 160 sets a Boolean variable (ATAF_DATA) equal to true (230). However, when either condition is not satisfied in such examples ("NO" branch of step 228), the comparison module 160 sets the AT/AF variable equal to false (232).

Diagnostic module 120 uses the secondary parameter data, e.g., the Boolean variable to determine whether the secondary diagnostic parameters satisfy the predetermined condition (186 of FIG. 9), e.g., when the variable is true, to detect worsening heart failure in patient 14. In some examples, diagnostic module 120 does not maintain a Boolean variable (ATAF_DATA), but instead determines whether both conditions are satisfied in response to determining that the fluid index is within the threshold zone (182 and 184 of FIG. 9). The various values and counters discussed with respect to FIG. 11 may be modified on periodic basis, e.g., hourly or daily, and the example method of FIG. 11 may also be performed on a periodic basis. The various values, e.g., AT/AF burden values, may be daily values, weekly values, or the like, and may be average or median values.

Figure 12:
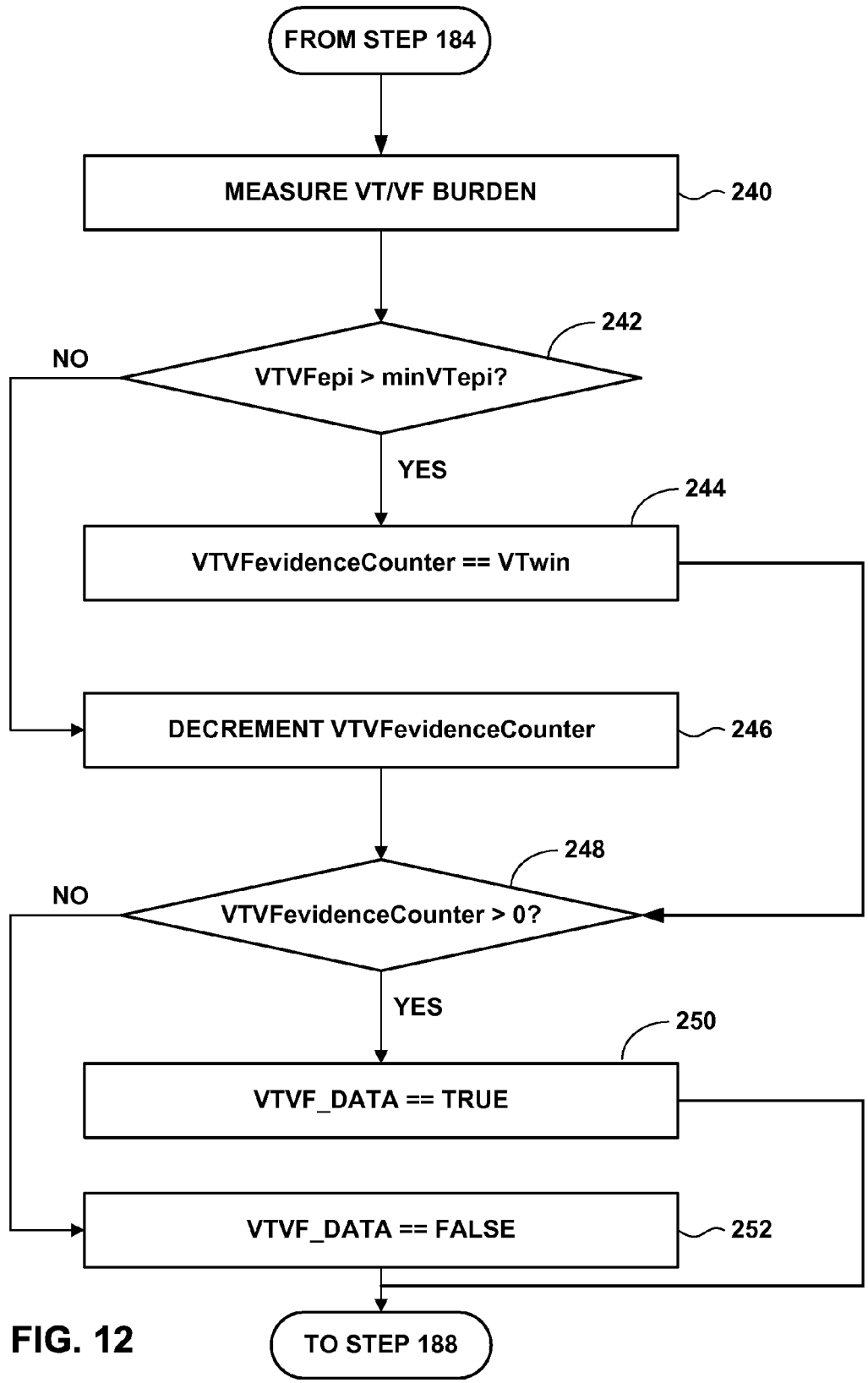

FIG. 12 is a flow diagram illustrating an example method for determining whether a patient is experiencing worsening heart failure based on ventricular tachycardia and ventricular fibrillation in patient 14. The method illustrated in FIG. 12 begins with secondary parameter unit 124 determining a VT/VF burden value (240). In particular in this example, secondary parameter unit 124 determines a number of VT and/or VF episodes. The number of VT/VF episodes may be a daily (or weekly or monthly) total, or an average or median of a number of such totals, e.g., of the totals for the previous N days. In other examples, a VT/VF burden value may be determined based on the duration of the episodes, or the ventricular rate during such episodes, as examples.

Comparison module 160 may compare the number of episodes (VTVFepi) to a threshold value (minVTepi) (242). When the number of measured VT/VF episodes is greater than the threshold value ("YES" branch of step 242), comparison module 160 sets the value of a count variable (VTVFevidenceCounter) equal to a predetermined value (VTwin) (244). On the other hand, each day (or other period) when the number of measured VT/VF episodes is not greater than the threshold value ("NO" branch of step 242), comparison module 160 decrements the count variable (246).

In some examples, comparison module 160 may additionally consider the ventricular rate during VT/VF, e.g., determine whether the VT/VF burden was greater than a threshold number of hours and the ventricular rate during the VT/VF was greater than a threshold rate, to determine whether to set or decrement the VT/VF counter. In other examples, only VT/VF associated with a threshold ventricular rate may be counted as VT/VF burden for setting or decrementing the counter.

To determine whether the VT/VF condition corroborates the primary diagnostic parameter evidence indicating worsening heart failure in patient 14, comparison module 160 compares the count variable to a corresponding threshold value (248). In the illustrated example the threshold value is equal to zero. Accordingly, if the count variable is greater than zero ("YES" branch of step 248), then comparison module 160 sets the secondary parameter data, e.g., Boolean variable VTVF_DATA equal to true (250). However if the count variable is not greater than zero ("NO" branch of step 248), comparison module 160 sets the secondary parameter data value equal to false (252).

Diagnostic module 120 uses the secondary parameter data, e.g., the Boolean variable, to determine whether the secondary diagnostic parameters satisfy the predetermined condition (186 of FIG. 9 to detect worsening heart failure in patient 14. In some examples, diagnostic module 120 does not maintain a Boolean variable (VTVF_DATA), but instead determines whether VTVFevidenceCounter is greater than the threshold, e.g., zero, in response to determining that the fluid index is within the threshold zone (182 and 184 of FIG. 9).

Figure 13:
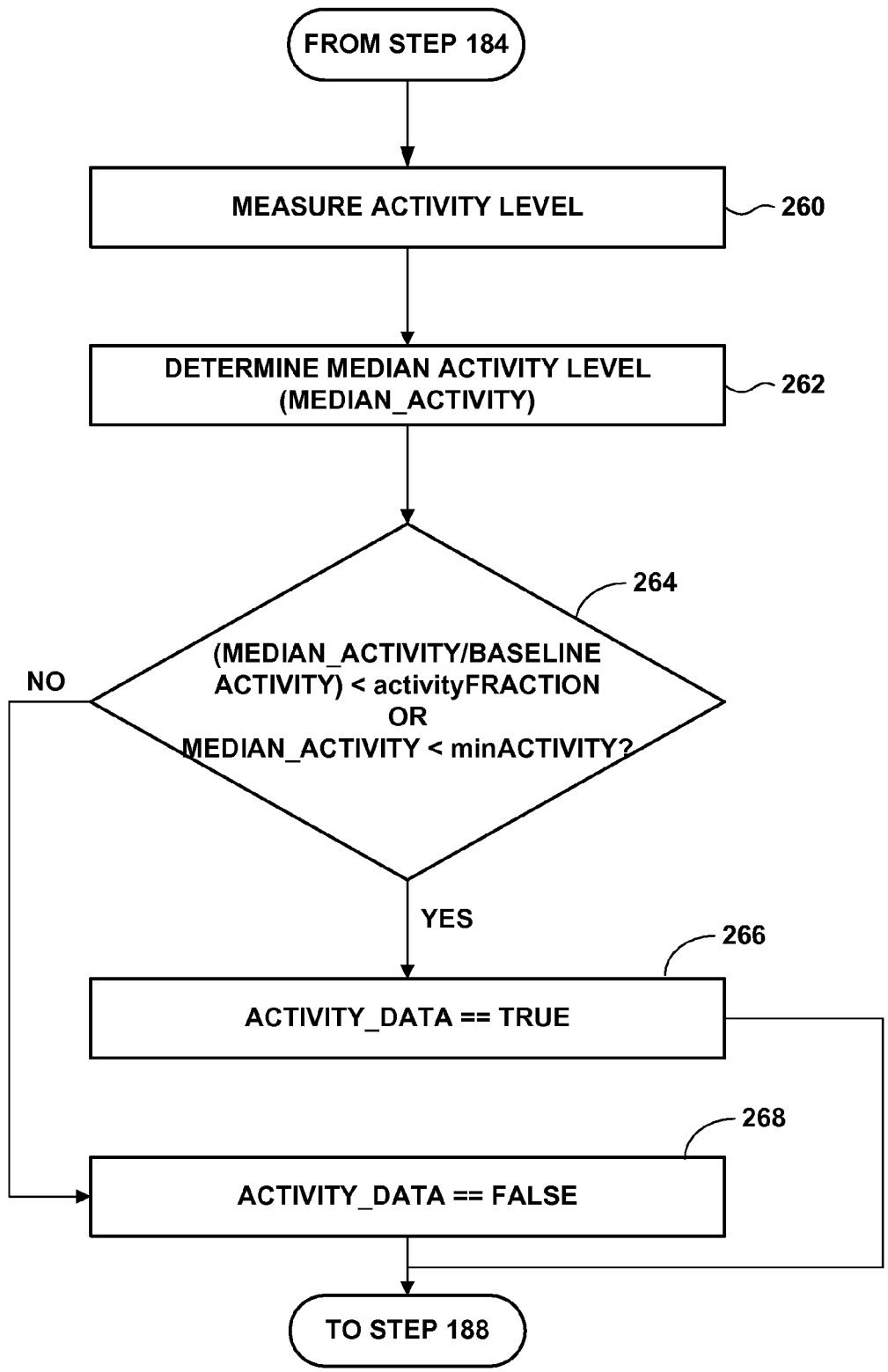

FIG. 13 is a flow diagram illustrating an example method for determining whether a patient is experiencing worsening heart failure based on the activity level of patient 14. Initially, secondary parameter unit 124 receives a signal, e.g., from a sensor 91, or data that indicates an activity level of patient 14 (260). In some embodiments, the activity level of patient 14 may be measured at periodic intervals throughout the day or over a portion of the day. Multiple measurements may be averaged to obtain a daily value, or a value associated with some other period greater than the measurement frequency. Next, secondary parameter unit 124 may determine a median activity level (MEDIAN_ACTIVITY) of patient 14 (262). The median value may be determined as the median of the last "X" number of daily (or some other period) average activity level values.

Comparison module 160 determines the ratio of the median activity level to a baseline activity level, and compares the ratio to a first threshold value (activityFRACTION) and the median activity level to another threhsold value (minACTIVITY) (264). The baseline activity level may be defined as the median activity level prior to the fluid index entering the threshold zone. The activityFRACTION threshold value may be computed as a predetermined or variable fraction of the previous median activity level, i.e., the median activity level prior to inclusion of the current daily value.

In this manner, a secondary diagnostic parameter, in this case activity level, may be compared to both an absolute threshold, in this case minAcCTIVITY, which indicates whether the parameter has reached a level at which it is considered indicative of worsening heart failure, and a threshold that indicates a rate of change, in this case activityFRACTION, which indicates whether the parameter has changed at a rate that considered indicative of worsening heart failure. Other secondary parameters, such as heart rate variability and night heart rate, which are discussed below, may be similarly compared to multiple thresholds, which may be absolute and related to a rate of change.

When the current median activity level is less than either of these threshold values, the activity level condition is satisfied ("YES" branch of step 264), and comparison module 160 sets the secondary parameter data equal to true (266). However, when both conditions are not satisfied ("NO" branch of step 264), comparison module 160 sets the secondary parameter data value equal to false (268). In some examples, the analysis of activity level may include use of an activity level index similar to the fluid index, which may accumulate over time as the median activity or ratio of median to baseline activity is less than an adaptive threshold, such as activity fraction. The index may be compared to a threshold to determine whether to set the secondary parameter data value to a true or false value. Secondary parameter unit 124 outputs the secondary parameter data to diagnostic module 120 in diagnostic unit 92 for use in step 188 (FIG. 9) to detect worsening heart failure in patient 14.

Diagnostic module 120 uses the secondary parameter data, e.g., the Boolean variable, to determine whether the secondary diagnostic parameters satisfy the predetermined condition (186 of FIG. 9 to detect worsening heart failure in patient 14. In some examples, diagnostic module 120 does not maintain a Boolean variable, but instead determines whether the median activity level is less than one or more thresholds in response to determining that the fluid index is within the threshold zone (182 and 184 of FIG. 9).

Figure 14:
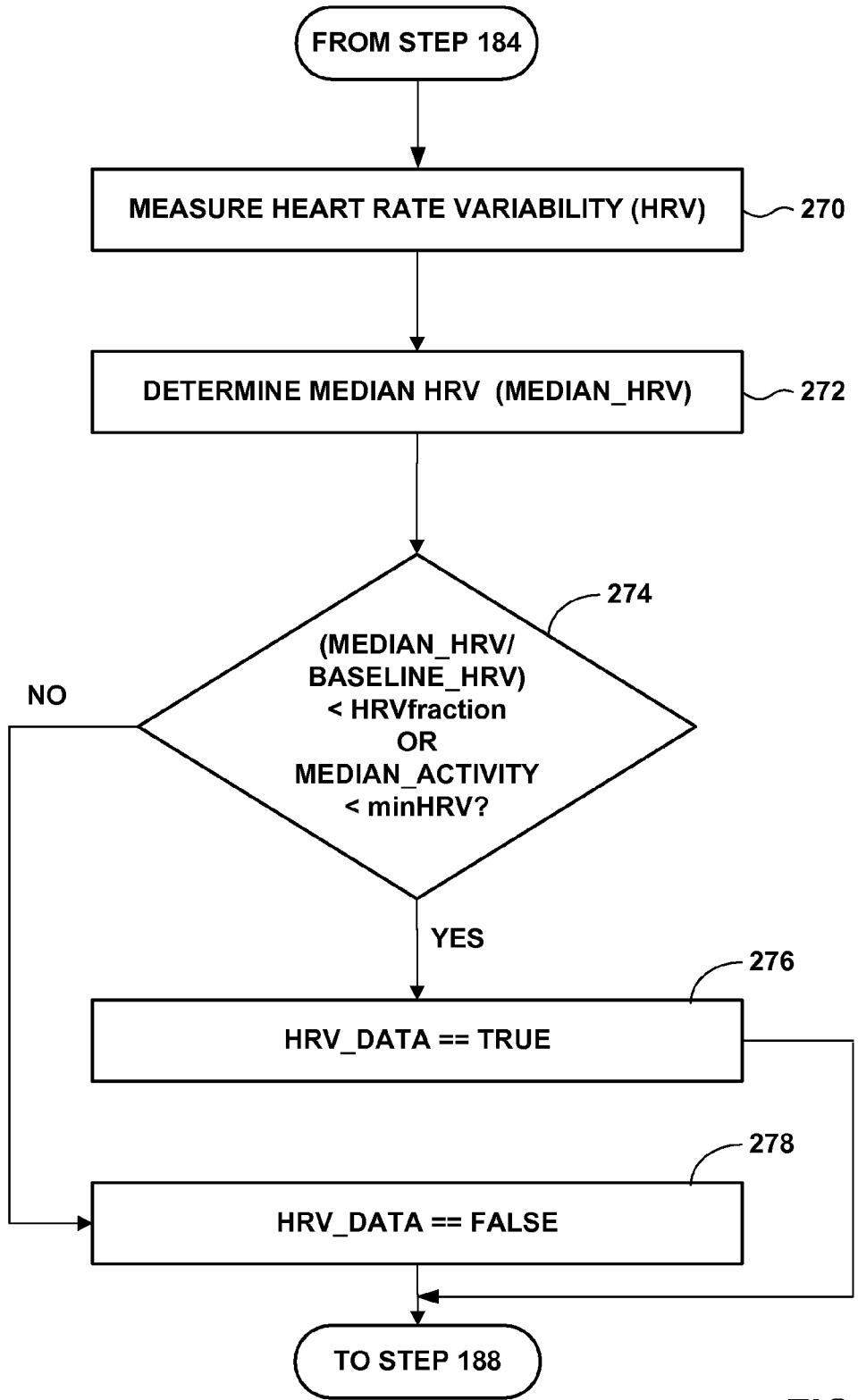

FIG. 14 is a flow diagram illustrating an example method for determining whether a patient is experiencing worsening heart failure based on the heart rate variability (HRV) of patient 14. Initially, secondary parameter unit 124 determines a HRV value for patient 14 based on, for example, ventricular rate information received from electrical sensing module 86 and/or processor 80 (FIG. 3) (270). Similar to the activity level of patient 14, the HRV of patient 14 may be a daily (or other period) value, e.g., the variability of a plurality of heart rates determined over the course of a day. Similar to the activity level of patient 14, secondary parameter unit 124 may determine a median HRV value (MEDIAN_HRV) of patient 14 (272) as the median of the last "X" number of daily (or other period) HRV values. Secondary parameter unit 124 may also determine a baseline HRV value Comparison module 160 determines the ratio of the median HRV to a baseline HRV, and compares the ratio to a first threshold value (HRVfraction) and the median HRV to a second threshold value (minHRV) (274). The baseline HRV may be defined as the median HRV prior to the fluid index entering the threshold zone. The HRVfraction value may be computed as a predetermined or variable fraction of the previous median HRV, e.g., the median HRV prior to inclusion of the current daily value. When either condition is satisfied ("YES" branch of step 274), comparison module 160 sets the secondary parameter data equal to true (276). That is, when the median HRV value is less than HRVfraction or when the median HRV value is less than minHRV, comparison module 160 sets the Boolean variable ACTIVITY_DATA equal to zero. However, when both conditions are not satisfied ("NO" branch of step 274), control logic 178 sets the secondary parameter data value equal to false (278). In some examples, the analysis of HRV may include use of an HRV index similar to the fluid index, which may accumulate over time as the median HRV or ratio of median to baseline HRV is less than an adaptive threshold, such as HRVfraction. The index may be compared to a threshold to determine whether to set the secondary parameter data value to a true or false value.

Diagnostic module 120 uses the secondary parameter data, e.g., the Boolean variable, to determine whether the secondary diagnostic parameters satisfy the predetermined condition (186 of FIG. 9 to detect worsening heart failure in patient 14. In some examples, diagnostic module 120 does not maintain a Boolean variable, but instead determines whether the median activity level is less than one or more thresholds in response to determining that the fluid index is within the threshold zone (182 and 184 of FIG. 9).

Figure 15:
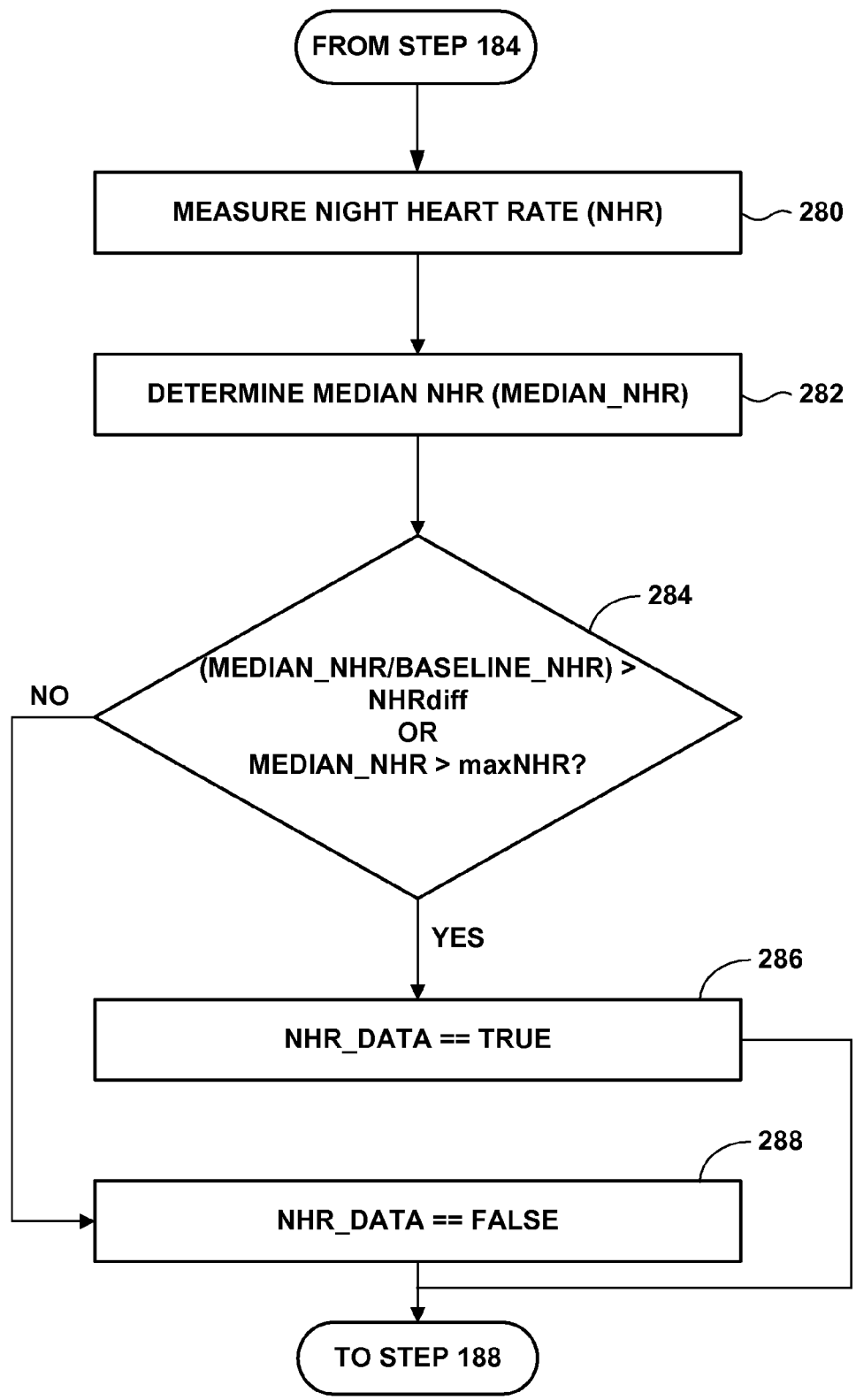

FIG. 15 is a flow diagram illustrating an example method for determining whether a patient is experiencing worsening heart failure based on the night heart rate (NHR) of patient 14. Although illustrated with respect to night heart rate, this method may be similarly applied to other secondary diagnostic parameters, such as the difference between day and night heart rate, alone or in conjunction with NHR. In general, the difference between day and night heart rate may satisfy a secondary diagnostic parameter condition, and thereby indicated worsening heart failure, when it is less than a threshold rate. The threshold may be absolute, adaptive, or may involve multiple thresholds, which may be absolute or adaptive.

With respect to NHR and the example of FIG. 15, initially, secondary parameter unit 124 determines the NHR of patient 14 (280), e.g., based on ventricular rate information received from electrical sensing module 86 and/or processor 80 (FIG. 3) at night. The NHR of patient 14, similar to the activity level and HRV of patient 14, may be measured at periodic intervals throughout the night, and a daily (or other period) average may be determined. Secondary parameter unit 124 may determine a median NHR value (MEDIAN_NHR) of patient 14 (282). The median value may be determined as the median of the last "X" number of daily (or other period) NHR values.

Comparison module 160 determines the ratio of the median NHR to a baseline NHR, and compares the ratio to a first threshold (NHRdiff), and compares the median NHR value to a second threshold value (maxNHR) (284). The baseline NHR may be defined as the median NHR prior to the fluid index entering the threshold zone. The NHRdiff value may be as an example, 20 beats per minute, or any value that would represent a clinically significant increase in NHR. When either condition is satisfied ("YES" branch of step 274), comparison module 160 sets the secondary parameter data equal to true (286). However, when both conditions are not satisfied ("NO" branch of step 264), comparison module 160 sets the secondary parameter data value equal to false (268). In some examples, the analysis of NHR may include use of an NHR index similar to the fluid index, which may accumulate over time as the median NHR or ratio of median to baseline NHR is greater than an adaptive threshold. The index may be compared to a threshold to determine whether to set the secondary parameter data value to a true or false value.

Diagnostic module 120 uses the secondary parameter data, e.g., the Boolean variable, to determine whether the secondary diagnostic parameters satisfy the predetermined condition (186 of FIG. 9 to detect worsening heart failure in patient 14. In some examples, diagnostic module 120 does not maintain a Boolean variable, but instead determines whether the median activity level is less than one or more thresholds in response to determining that the fluid index is within the threshold zone (182 and 184 of FIG. 9).

Figure 16:
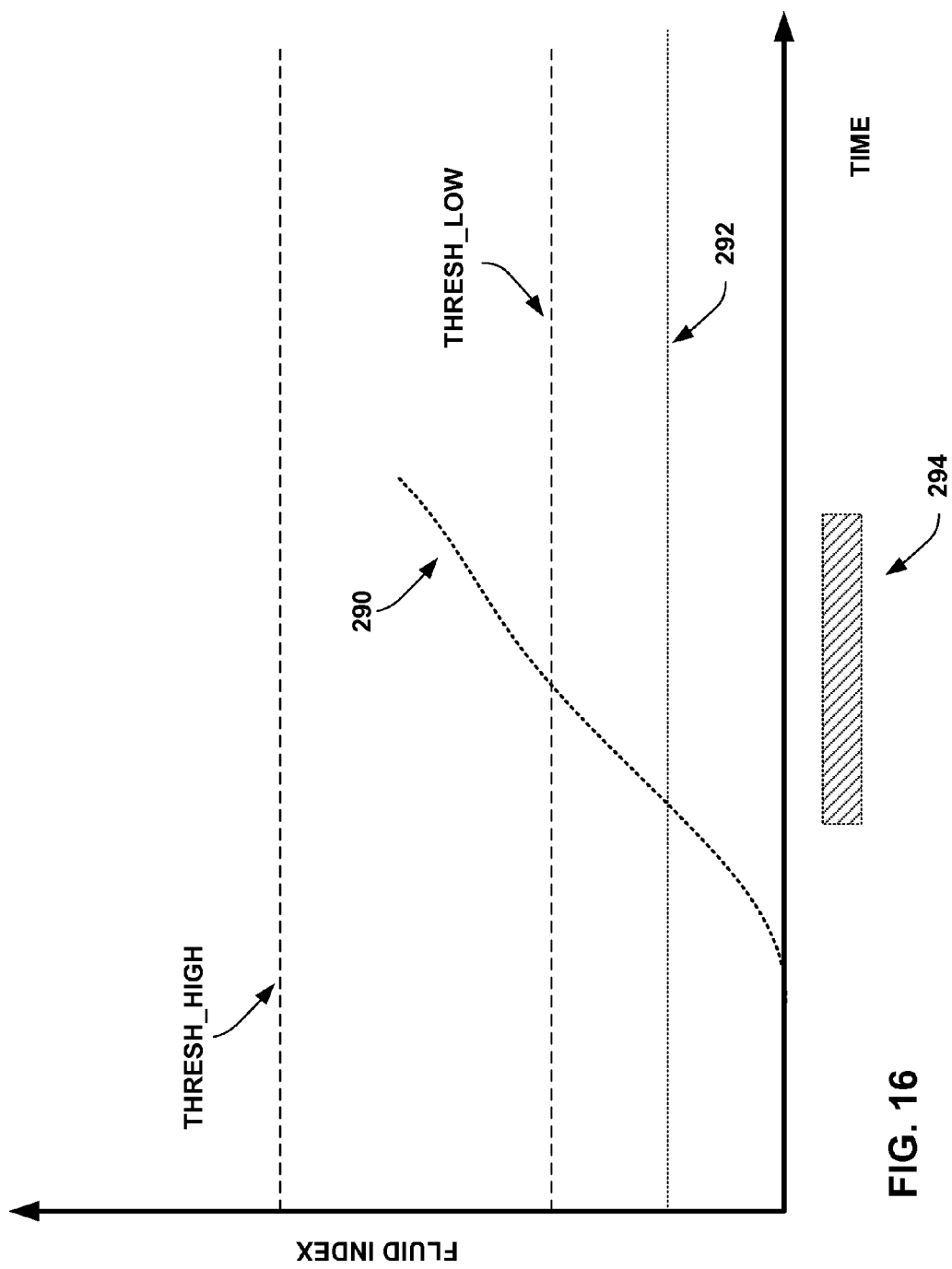
FIG. 16 is a graph illustrating an example of a fluid index that increments over time relative to an example threshold zone.

FIG. 16 is a graph illustrating an example of a fluid index 290 that increments over time relative to an example threshold zone. As illustrated in FIG. 16, the threshold zone is defined by a higher and lower threshold (THRESH_HIGH and THRESH_LOW), e.g., as being between the thresholds. When fluid index 290 is within the threshold zone, e.g., between the thresholds, as shown in FIG. 16, diagnostic module 120 looks to the one or more secondary diagnostic parameters to determine whether the patient is experiencing worsening heart failure.

FIG. 16 also illustrates a secondary diagnostic parameter monitoring threshold 292, and an observation window 294. In some examples, an IMD or other device may begin monitoring secondary diagnostic parameters when the fluid index meets threshold 292, such that the observation window 294 includes some time prior to entry into the threshold zone. In this manner, the analysis of the secondary parameters may include data prior to entry into the threshold zone, such as medians of secondary diagnostic parameters prior to entry into the zone that may be used as baselines, e.g., FIGS. 13-15.

Figure 17:
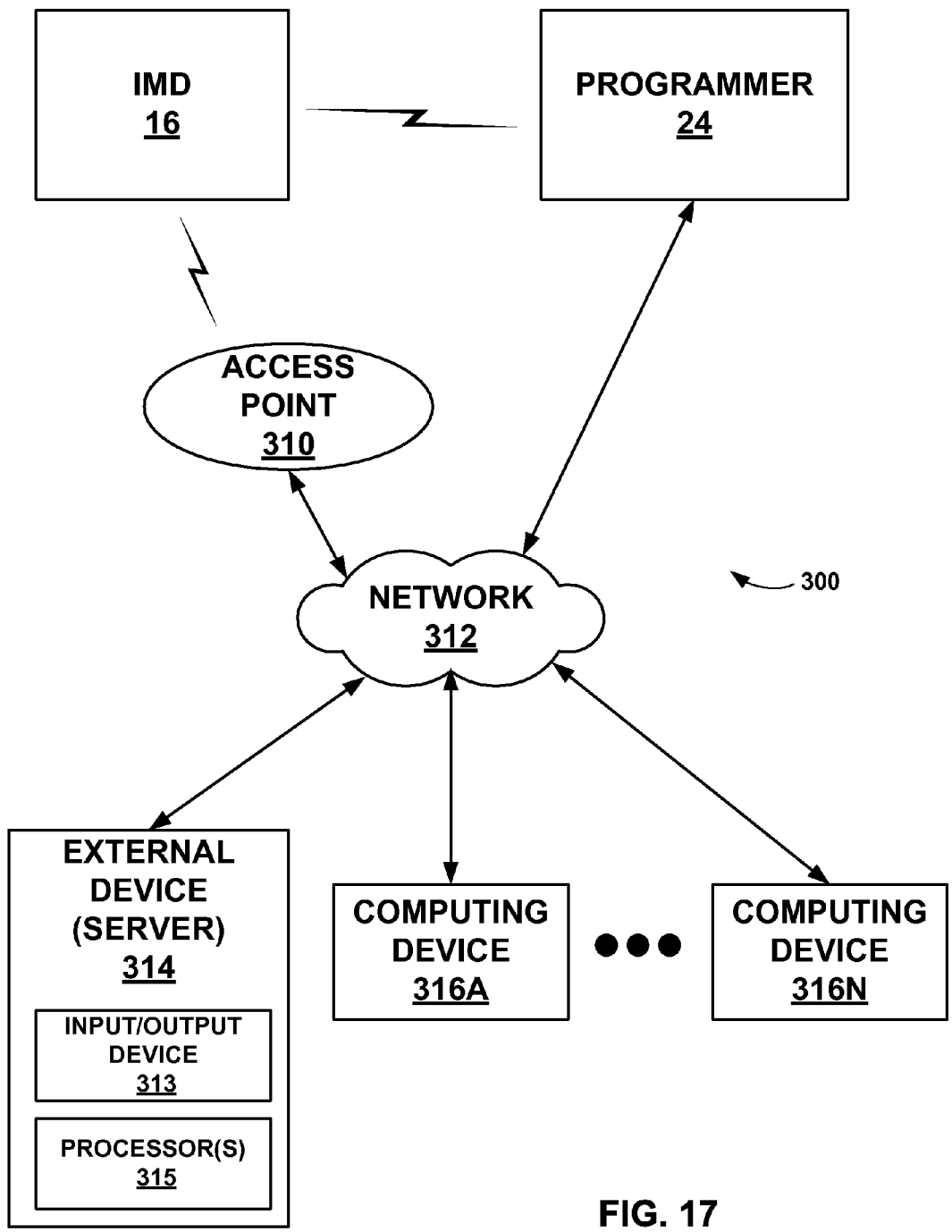
FIG. 17 is a block diagram illustrating an example system that includes an external device, such as a server, and one or more computing devices that are coupled to the IMD and programmer shown in FIG. 1 via a network.

FIG. 17 is a block diagram illustrating an example system 300 that includes an external device, such as a server 314, and one or more computing devices 316A-316N ("computing devices 316") that are coupled to IMD 16 and programmer 24 shown in FIG. 1 via a network 312. In this example, IMD 16 may use its telemetry module 88 to communicate with programmer 24 via a first wireless connection, and to communication with an access point 310 via a second wireless connection. In the example of FIG. 17, access point 310, programmer 24, server 314, and computing devices 316A-216N are interconnected, and able to communicate with each other, through network 312. In some cases, one or more of access point 310, programmer 24, server 314, and computing devices 316A-316N may be coupled to network 312 through one or more wireless connections. IMD 16, programmer 24, server 314, and computing devices 316A-216N may each comprise one or more processors, such as one or more microprocessors, DSPs, ASICs, FPGAs, programmable logic circuitry, or the like, that may perform various functions and operations, such as those described herein. For example, as illustrated in FIG. 17, server 314 may comprise one or more processors 315 and an input/output device 313, which need not be co-located.

Server 314 may, for example, monitor primary and secondary diagnostic parameters, e.g., based on signals or information received from IMD 16 and/or programmer 24 via network 312, to detect worsening heart failure of patient 14 using any of the techniques described herein. Server 314 may provide alerts relating to worsening heart failure of patient 16 via network 312 to patient 14 via access point 310, or to one or more clinicians via computing devices 316. In examples such as those described above in which IMD 16 and/or programmer 24 monitor the primary and secondary diagnostic parameters, server 314 may receive an alert from the IMD or programmer via network 312, and provide alerts to one or more clinicians via computing devices 316. Server 314 may generate web-pages to provide alerts and information regarding the primary and secondary diagnostic parameters, and may comprise a memory to store alerts and diagnostic or physiological parameter information for a plurality of patients.

Access point 310 may comprise a device that connects to network 312 via any of a variety of connections, such as telephone dial-up, digital subscriber line (DSL), or cable modem connections. In other embodiments, access point 310 may be coupled to network 312 through different forms of connections, including wired or wireless connections. Network 312 may comprise a local area network, wide area network, or global network, such as the Internet. System 300 may be implemented, in some aspects, with general network technology and functionality similar to that provided by the Medtronic CareLink® Network developed by Medtronic, Inc., of Minneapolis, Minn.

Additionally, using programmers 24, access points 310 or computing devices 316, physicians and/or event patients may input clinical information regarding the patients (such as symptoms, lab results, health care utilizations, etc.) that may be used as secondary parameters by the detection algorithm. Furthermore, the functionality described herein with respect to monitoring worsening heart failure may be provided by any one or more of the programmers 24, access points 310, server 314, or computing devices 316.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. However, one of ordinary skill in the art will appreciate that various modifications may be made to the described examples without departing from the scope of the claims. For example, although described primarily with reference to intrathoracic impedance, in some examples a cardiovascular pressure may additionally or alternatively be used as a primary diagnostic parameter. In some examples, a fluid index may increase based on increasing cardiovascular pressure over time, in a substantially similar manner to that which the fluid index discussed above increased based on decreasing intrathoracic impedance over time. Examples of cardiovascular pressures that may be monitored are right ventricular pressure, left atrial pressure, or estimated pulmonary artery diastolic pressure.

Furthermore, although described primarily with reference to examples that provide an alert in response to detecting worsening heart failure, other examples may additionally or alternatively automatically modify a therapy in response to detecting worsening heart failure in the patient. The therapy may be, as examples, a substance delivered by an implantable pump, cardiac resynchronization therapy, refractory period stimulation, or cardiac potentiation therapy. These and other examples are within the scope of the following claims.

The invention claimed is:

1. A method comprising:
   monitoring, by a processor, at least one primary diagnostic parameter and at least one secondary diagnostic parameter of a patient, wherein the primary and secondary diagnostic parameters are associated with worsening heart failure;
   changing, by the processor, an index value over time based on the primary diagnostic parameter, wherein the index indicates worsening heart failure of the patient;
   determining, by the processor, whether the index is within a threshold zone defined by a lower threshold and an upper threshold;
   detecting, by a processor, worsening heart failure in the patient when the index is greater than the upper threshold;
   and determining, by the processor, whether worsening heart failure is detected in the patient based on the secondary diagnostic parameter when the index is within the threshold zone.

2. The method of claim 1, further comprising determining that worsening heart failure is not detected in the patient when the index is less than the lower threshold.

3. The method of claim 1,
wherein monitoring at least one secondary diagnostic parameter comprises monitoring a plurality of secondary diagnostic parameters, and
wherein determining whether worsening heart failure is detected in the patient based on the secondary diagnostic parameter comprises determining whether worsening heart failure is detected in the patient when any of the secondary diagnostic parameters indicates worsening heart failure.

4. The method of claim 1, wherein the primary diagnostic parameter comprises intrathoracic impedance.

5. The method of claim 1, wherein the primary diagnostic parameter comprises cardiovascular pressure.

6. The method of claim 1, wherein the at least one secondary diagnostic parameter comprises one or more of atrial fibrillation (AF) burden, ventricular rate during AF, ventricular fibrillation (VF) burden, ventricular rate during VF, atrial tachyarrhythmia (AT) burden, ventricular rate during AT, ventricular tachyarrhythmia (VT) burden, or ventricular rate during VT.

7. The method of claim 1, wherein the at least one secondary diagnostic parameter comprises one or more of activity level, heart rate variability, percentage of cardiac resynchronization pacing, night heart rate, difference between day heart rate and night heart rate, heart rate turbulence, heart rate deceleration capacity, or baroreflex sensitivity.

8. The method of claim 1, wherein the at least one secondary diagnostic parameter comprises one or more of respiratory rate, respiratory depth, or respiratory pattern.

9. The method of claim 1, wherein the at least one secondary diagnostic parameter comprises one or more of weight, blood pressure, metrics of renal function, medication history, or history of heart failure hospitalization.

10. The method of claim 1, wherein the threshold zone is static over time.

11. The method of claim 1, further comprising changing the threshold zone over time.

12. The method of claim 11, wherein changing the threshold zone over time comprises at least one of automatically changing a size of the threshold zone, or automatically changing a range of the threshold zone.

13. The method of claim 11, wherein dynamically changing the threshold zone comprises automatically changing the threshold zone as a function of time.

14. The method of claim 1,
wherein determining whether worsening heart failure is detected in the patient based on the secondary diagnostic parameter comprises comparing the secondary diagnostic parameter to a first threshold and a second threshold,
wherein the first threshold is a predetermined constant threshold, the second threshold is variable, and comparison of the secondary diagnostic parameter to the second threshold indicates a rate of change of the secondary diagnostic parameter.

15. The method of claim 1, further comprising generating an alert in response to detecting worsening heart failure in the patient.

16. The method of claim 1, further comprising automatically modifying a therapy delivered to the patient in response to detecting worsening heart failure in the patient.

17. The method of claim 16, wherein the therapy comprises at least one of a substance delivered by an implantable pump, cardiac resynchronization therapy, refractory period stimulation, or cardiac potentiation therapy.

18. The method of claim 1, wherein the index comprises a fluid index that indicates fluid accumulation of the patient.

19. The method of claim 1, wherein monitoring at least one secondary diagnostic parameter of the patient comprises monitoring the at least one secondary diagnostic parameter when the index is greater than a secondary diagnostic parameter monitoring threshold that is less than the lower threshold.

20. The method of claim 19, wherein monitoring at least one secondary diagnostic parameter of the patient comprises monitoring the at least one secondary diagnostic parameter when the index is within a threshold zone defined by the secondary diagnostic parameter monitoring threshold and the upper threshold.

21. A system comprising:
at least one sensor; and
a processor that:
monitors at least one primary diagnostic parameter and at least one secondary diagnostic parameter of a patient based on at least one signal from the at least one sensor, wherein the primary and secondary diagnostic parameters are associated with worsening heart failure of the patient,
changes an index value over time based on the primary diagnostic parameter, wherein the index indicates worsening heart failure of the patient,
determines whether the index is within a threshold zone defined by a lower threshold and an upper threshold,
detects worsening heart failure in the patient when the index is greater than the upper threshold, and
determines whether worsening heart failure is detected in the patient based on the secondary diagnostic parameter when the index is within the threshold zone.

22. The system of claim 21, wherein the processor determines that worsening heart failure is not detected in the patient when the index is less than the lower threshold.

23. The system of claim 21, wherein the processor monitors a plurality of secondary diagnostic parameters, and determines whether worsening heart failure is detected in the patient when any of the secondary diagnostic parameters indicates worsening heart failure.

24. The system of claim 21, wherein the at least one sensor comprises a plurality of electrodes, and the primary diagnostic parameter comprises intrathoracic impedance.

25. The system of claim 21, wherein the at least one sensor comprises a pressure sensor, and the primary diagnostic parameter comprises cardiovascular pressure.

26. The system of claim 21, wherein the at least one sensor comprises a plurality of electrodes, and the at least one secondary diagnostic parameter comprises one or more of atrial fibrillation (AF) burden, ventricular rate during AF, ventricular fibrillation (VF) burden, ventricular rate during VF, atrial tachyarrhythmia (AT) burden, ventricular rate during AT, ventricular tachyarrhythmia (VT), or ventricular rate during VT.

27. The system of claim 21, wherein the at least one sensor comprises an accelerometer, and the at least one secondary diagnostic parameter comprises activity level.

28. The system of claim 21, wherein the at least one sensor comprises a plurality of electrodes, and the at least one secondary diagnostic parameter comprises one or more of heart rate variability, night heart rate, difference between day heart rate and night heart rate, heart rate turbulence, or heart rate deceleration capacity.

29. The system of claim 21, wherein the at least one sensor comprises a plurality of electrodes, and the at least one secondary diagnostic parameter comprises one or more of respiratory rate, respiratory depth, or respiratory pattern.

30. The system of claim 21, wherein the at least one secondary diagnostic parameter comprises one or more of percentage of cardiac resynchronization pacing, baroreflex sensitivity, weight, blood pressure, metrics of renal function, medication history, or history of heart failure hospitalization.

31. The system of claim 21, wherein the at least one sensor comprises at least one electrode located on an implantable medical lead coupled to an implantable medical device.

32. The system of claim 21, wherein the at least one sensor is at least one of within or coupled to an implantable medical device, and the processor comprises a processor of the implantable medical device.

33. The system of claim 32, further comprising an external device that wirelessly communicates with the implantable medical device, wherein the processor monitors the at least one secondary parameter based on information input by a user via the external device.

34. The system of claim 21, wherein the processor automatically changes the threshold zone as a function of time.

35. The system of claim 21,
wherein the processor compares the secondary diagnostic parameter to a first threshold and a second threshold,
wherein the first threshold is a predetermined constant threshold, the second threshold is variable, and comparison of the secondary diagnostic parameter to the second threshold indicates a rate of change of the secondary diagnostic parameter.

36. The system of claim 21, wherein the processor provides an alert to a user in response to detecting worsening heart failure in the patient.

37. The system of claim 21, further comprising an implantable medical device that delivers a therapy to the patient, wherein the processor automatically modifies the therapy in response to detecting worsening heart failure in the patient.

38. The system of claim 37, wherein the therapy comprises at least one of a substance delivered by an implantable pump, cardiac resynchronization therapy, refractory period stimulation, or cardiac potentiation therapy.

39. The system of claim 21, wherein the index comprises a fluid index that indicates fluid accumulation of the patient.

40. The system of claim 21, wherein the processor monitors the at least one secondary diagnostic parameter when the index is greater than a secondary diagnostic parameter monitoring threshold that is less than the lower threshold.

41. The system of claim 40, wherein the processor monitors the at least one secondary diagnostic parameter when the index is within a threshold zone defined by the secondary diagnostic parameter monitoring threshold and the upper threshold.

42. A computer-readable medium comprising instructions that cause a processor to:
monitor at least one primary diagnostic parameter and at least one secondary diagnostic parameter of a patient, wherein the primary and secondary diagnostic parameters are associated with worsening heart failure;
change an index value over time based on the primary diagnostic parameter, wherein the index indicates worsening heart failure of the patient;
determine whether the index is within a threshold zone defined by a lower threshold and an upper threshold;
detect worsening heart failure in the patient when the index is greater than the upper threshold;
and
determine whether worsening heart failure is detected in the patient based on the secondary diagnostic parameter when the index is within the threshold zone.

43. A system comprising:
means for monitoring at least one primary diagnostic parameter and at least one secondary diagnostic parameter of a patient, wherein the primary and secondary diagnostic parameters are associated with worsening heart failure;
means for changing an index value over time based on the primary diagnostic parameter, wherein the index indicates worsening heart failure of the patient;
means for determining whether the index is within a threshold zone defined by a lower threshold and an upper threshold;
means for detecting worsening heart failure in the patient when the index is greater than the upper threshold;
and
means for determining whether worsening heart failure is detected in the patient based on the secondary diagnostic parameter when the index is within the threshold zone.

* * * * *